US012601801B2

(12) United States Patent
Woolger et al.

(10) Patent No.: US 12,601,801 B2
(45) Date of Patent: Apr. 14, 2026

(54) MAGNETIC SHIELD

(71) Applicants: MAGNETIC SHIELDS LIMITED, Tonbridge (GB); UNIVERSITY OF NOTTINGHAM, Nottingham (GB)

(72) Inventors: David Woolger, Tonbridge (GB); James Chalmers, Tonbridge (GB); Joseph Farmer, Tonbridge (GB); Eliot Dawson, Tonbridge (GB); Richard Bowtell, Nottingham (GB); Matthew Brookes, Nottingham (GB); Niall Holmes, Nottingham (GB); Paul Glover, Nottingham (GB)

(73) Assignees: MAGNETIC SHIELDS LIMITED, Staplehurst (GB); UNIVERSITY OF NOTTINGHAM, Nottingham (GB)

( * ) Notice: Subject to any disclaimer, the term of this patent is extended or adjusted under 35 U.S.C. 154(b) by 156 days.

(21) Appl. No.: 18/559,627

(22) PCT Filed: May 20, 2022

(86) PCT No.: PCT/EP2022/063808
§ 371 (c)(1),
(2) Date: Nov. 8, 2023

(87) PCT Pub. No.: WO2022/238588
PCT Pub. Date: Nov. 17, 2022

(65) Prior Publication Data
US 2024/0280657 A1 Aug. 22, 2024

(30) Foreign Application Priority Data

May 14, 2021 (GB) ...................................... 2106961
Jun. 30, 2021 (GB) ...................................... 2109459

(51) Int. Cl.
*G01R 33/421* (2006.01)
*A61B 5/055* (2006.01)
(Continued)

(52) U.S. Cl.
CPC .......... *G01R 33/4215* (2013.01); *A61B 5/055* (2013.01); *A61B 5/245* (2021.01);
(Continued)

(58) Field of Classification Search
CPC .. G01R 33/4215; G01R 33/025; A61B 5/055; A61B 5/245; A61B 2562/0223; A61B 2562/182; H05K 9/0071
See application file for complete search history.

(56) References Cited

U.S. PATENT DOCUMENTS 4,788,502 A 11/1988 Keller et al.
4,978,920 A 12/1990 Mansfield et al.
(Continued)

FOREIGN PATENT DOCUMENTS

CN 107831462 A 3/2018
JP 2000037362 A * 2/2000
(Continued)

OTHER PUBLICATIONS

Livanainen et al., On-scalp MEG system utilizing an actively shielded array of optically-pumped magnetometers. Neuroimage. Jul. 1, 2019;194:244-25 (Year: 2019).*
(Continued)

*Primary Examiner* — Daniel R Miller
(74) *Attorney, Agent, or Firm* — Westman, Champlin & Koehler, P.A

(57) ABSTRACT
An active magnetic shield system, including an array of magnetic field sensors arranged to sense a local magnetic field. An array of magnetic field elements are arranged produce a magnetic field. Each magnetic field element has a
(Continued)

unit coil for mounting to a plurality of surfaces arranged in at least 3 planes to define an enclosed cancellation volume, and to produce a vector magnetic field pattern.

20 Claims, 27 Drawing Sheets

(51) Int. Cl.
    *A61B 5/245*         (2021.01)
    *H05K 9/00*         (2006.01)

(52) U.S. Cl.
    CPC .... *H05K 9/0071* (2013.01); *A61B 2562/0223* (2013.01); *A61B 2562/182* (2013.01)

(56)                References Cited

U.S. PATENT DOCUMENTS

| | | | |
|---|---|---|---|
| 6,049,207 A | 4/2000 | Petropoulos | |
| 6,236,203 B1 | 5/2001 | Shvartsman et al. | |
| 9,030,197 B1 | 5/2015 | Meske et al. | |
| 2008/0294386 A1* | 11/2008 | Taulu ..................... | A61B 5/245 |
| | | | 702/191 |
| 2013/0197838 A1* | 8/2013 | Simola ................. | A61B 5/0035 |
| | | | 702/65 |
| 2013/0271145 A1* | 10/2013 | Hwang ................ | A61B 5/0046 |
| | | | 324/322 |
| 2014/0077612 A1 | 3/2014 | Onuma et al. | |
| 2015/0069846 A1 | 3/2015 | Hokari | |
| 2020/0348369 A1 | 11/2020 | Garber et al. | |
| 2021/0244328 A1* | 8/2021 | Kates-Harbeck ...... | A61B 5/245 |
| 2021/0369165 A1* | 12/2021 | Alford ................... | A61B 5/243 |

FOREIGN PATENT DOCUMENTS

| | | | |
|---|---|---|---|
| JP | 2003273565 A | | 9/2003 |
| JP | 2005217341 A | * | 8/2005 |
| JP | 2006324651 A | | 11/2006 |
| WO | 9001861 A1 | | 2/1990 |

OTHER PUBLICATIONS

Great Britain Combined Search and Examination Report Under Sections 17 & 18(3) dated Nov. 26, 2021 for GB2106961.2, filed May 14, 2021, 3 Pages.

Great Britain Search Report Under Section 17 dated Nov. 25, 2021 for GB2106961.2, filed May 14, 2021. 1 Page.

Great Britain Patents Act 1977, Further Search Report under Section 17 dated Jun. 5, 2022 for GB2109459.4, filed Jun. 30, 2021. 2 Pages.

* cited by examiner

A-A

40

41

40

40

45

48

46

47

44

A-A

50

51

50

50

55

58

56

57

54

A-A

80

81

80

80          85          88

86

87

84

MAGNETIC SHIELD

This application is a Section 371 United States National Phase entry from International Application PCT/EP2022/063808, filed May 20, 2022, published at WO 2022/238588; which claims the benefit of priority from Great Britain application 2106961.2, filed May 14, 2021, and which claims the benefit of priority from Great Britain application 2109459.4, filed Jun. 30, 2021. The contents of these priority applications are hereby incorporated by reference in their entireties.

FIELD OF THE INVENTION

The present invention relates to magnetic shielding systems. More specifically, the present invention relates to the design, optimisation and operating principle of an active magnetic shielding system.

BACKGROUND ART

The shielding of sensors and equipment from magnetic fields is critical in many applications, including fundamental physics experiments and satellite measurements. Such shielding is also crucial in medical imaging, including magnetoencephalography (MEG) and magnetic resonance imaging (MRI).

Magnetic shields fall into two types; active shields and passive shields. Passive shielding is achieved by blocking a magnetic field with barriers of conductive or magnetic materials to isolate a shielded space. For static or slowly varying magnetic fields, permalloy or mu-metal shields are used to provide a path for the magnetic shield lines around a shielded volume.

The most effective shape for a magnetic shield is therefore that of a closed container surrounding a shielded volume.

To shield beyond the limits of passive shielding, active shielding may also be used within a passively shielded volume. Active shielding uses a field created by electromagnets to cancel the ambient field within a volume by producing a counter field that matches the geometry of the ambient field.

The human brain can be thought of as a highly complex electrical circuit, containing hundreds of billions of current-carrying neurons. Just like electric currents flowing through wires, the tiny currents that flow through neurons generate magnetic fields. If these magnetic fields are measured, a unique insight into brain function with millimetre precision can be obtained, and used to identify clinical markers such as the site of epileptic activity. Millisecond temporal resolution can also be obtained, and utilised in the study of real-time changes in brain state in response to environment.

Magnetoencephalography (usually known as MEG) measures the magnetic fields generated by the brain non-invasively using arrays of magnetic field sensors that are placed on or held near to the scalp.

Magnetic fields can also be measured from the heart (MCG), the spine (MSG), gut (MGG) and muscular system (MMG) in medical treatment and diagnostics environments. Such imaging processes are also suitable for imaging and analysis of body parts and ex-vivo nerves and such like. These applications essentially require a similar level of shielding.

MEG presents a significant engineering challenge as the magnetic fields from the brain are more than a hundred billion times smaller than the Earth's magnetic field, and many orders of magnitude smaller than other external sources of magnetic interference, such as the fields generated by electronic devices, cars, lifts, and mains electricity. Consequently, the magnetic signals produced by brain function may be obscured by environmental magnetic interference.

Magnetic fields are generally measured by surrounding the magnetic field by a magnetic field sensor in which the strength and field direction are calculated based on the effect of the magnetic field on the effect of the magnetic field on the magnets, coils, and/or electrical components of the magnetic field sensor. It should be noted that earth field sensors operate in the range of 10 pT to 1 mT.

Many systems, including MEG systems, electron microscopes, and equipment used in atomic physics experiments, can be shielded from external sources of magnetic interference by a passive shield in the form of a magnetically shielded room (MSR), typically constructed from two or more layers of a material with a high magnetic permeability (e.g. a nickel-iron alloy such as mu-metal) and one layer of a material with a high electrical conductivity (e.g. copper or aluminium).

Until recently, all MEG systems, and similar, have used Superconducting QUantum Interference Devices (SQUIDs) for measuring magnetic fields from the brain. SQUIDs are low field sensors that detect low values of magnetic fields in the order of 1 fT (femtotesla).

SQUIDs are among the most sensitive magnetic field detectors available but require cryogenic cooling with liquid helium at −269° C. The associated costs and practical restrictions, including the necessary standardisation of design that is unsuitable for the scanning of participants with small heads, e.g. infants, and the need for the participant to be still during scanning, has significantly limited the uptake of MEG.

To make MEG systems more accessible, Optically Pumped Magnetometers (OPMs) have been used in place of SQUIDs in MEG systems. The miniaturisation and commercialisation of this kind of magnetic field sensor has enabled the development of wearable systems which can be adapted to many different scanning situations. OPM-MEG systems have been used to scan previously unsuitable subjects, including adult subjects who are moving, young children, and patients with conditions such as Parkinson's Disease and Tourette's Syndrome, for example, to take readings unattainable from a SQUID-MEG system.

OPM-MEG systems have inherent drawbacks, however. There is a significant difference between the SQUID and the OPM in the way they respond to static (or DC) magnetic fields, which vary very slowly with time (typically at frequencies<1 Hz).

SQUIDs are largely insensitive to static magnetic fields because they measure changes in time-varying or AC magnetic fields relative to a constant offset field. In contrast, OPMs operate around a 'zero-field resonance' and are only sensitive to magnetic fields within a narrow range of around ±5 nT (nanotesla).

The skilled reader will appreciate the difference in the order of magnitude between 5 nT ($10^{-9}$ T) and the strength of Earth's magnetic field at 50° latitude at 58 μT ($10^{-5}$ T).

State-of-the-art MSRs can reduce the magnetic field of the Earth and other interfering sources to around 2 nT, leaving a field that varies with spatial position at a rate of around 2 nT/m, but even in these reduced magnetic fields, small movements of the sensors on the head produce large changes in magnetic field which can easily exceed the dynamic range of the sensor resulting in signal loss.

Traditionally, active shielding systems of all applications have relied on simple coil designs such as orthogonal circular loops (known as a 'Helmholtz cage') which generate controlled magnetic field patterns over a fixed volume. A single Helmholtz coil typically consists of two identical circular magnetic coils that are placed symmetrically along a common axis, one on each side of the shielded volume, and separated by a distance equal to the radius of the coil. Each coil carries an equal electric current in the same direction. A Helmholtz coil can be used to cancel out the Earth's magnetic field inside a passive shield, producing a region with a magnetic field intensity much closer to zero It is difficult for the subject being scanned to physically get into and out of the enclosure formed by the Helmholtz coils, and the fixed nature of the cancellation arrangement restricts available movements and experiments. Bi-planar designs where coil windings are restricted to two planes can be generated, but these require the manufacturing of at least eight layers of intricate wire paths. Furthermore, the cancellation volume remains fixed, producing an inflexible system ill-suited to large unpredictable movements.

Interactions between the magnetic fields generated by active shielding coils and the high-permeability materials used in the construction of the MSR lead to distortions in the produced fields from their expected shapes and a change in the ratio of produced field strength to applied coil current which leads to poor shielding. Though these interactions can be incorporated into coil designs, the resulting systems remain limited to a fixed cancellation region.

SUMMARY OF THE INVENTION

The present invention relates to a magnetic field control system arranged to generate a known magnetic field. An embodiment of the invention provides a magnetic shielding system arranged to reduce the remnant magnetic field in MSRs and minimise loss of signal during subject movement in magnetic shielding devices.

The present invention therefore provides an active magnetic shield system comprising an array of magnetic field sensors arranged to sense a local magnetic field, an array of magnetic field elements arranged produce a magnetic field of −20 nT to +20 nT, each magnetic field element comprising a unit coil for mounting to a plurality of surfaces arranged in at least 3 planes to define an enclosed cancellation volume. Each unit coil comprises a coil wire path arranged to produce a vector magnetic field pattern, and a current source is arranged to provide a controlled current to each unit coil. A feedback algorithm is arranged for controlling the current source for each unit coil to minimise the sensed local magnetic field.

The unit coils may be arranged in three planes to define an enclosed cancellation volume, but can be arranged in up to 6 planes, according to the size and shape of the cancellation volume.

The active magnetic shield system may further comprise a passive magnetic shield arranged to support the array of magnetic field elements. The passive magnetic shield can comprise at least a first layer formed of high magnetic permeability material, and a further layer formed of high electrical conductivity material. The passive magnetic shield may also comprise a magnetically shielded room (MSR), wherein the array of magnetic field elements is placed on or in each wall of the MSR. Preferably, the magnetic field elements are affixed to an inner surface of each wall of the MSR.

The active magnetic shield system preferably produces a vector magnetic field pattern having a magnitude of 5 nT or smaller.

Preferably, each unit coil is a square coil. The square coils may be arranged in a two by two grid configuration in each of the three planes.

Preferably, the array of magnetic field elements comprises overlapping unit coils.

The active magnetic shield system may be arranged for use in magnetoencephalography (MEG) or MRI applications.

The present invention further provides method of producing an active magnetic shield. The method comprises generating a magnetic field by providing an array of magnetic field elements, each magnetic field element comprising a unit coil, specifying a set of coil parameters in each of the unit coils, applying current in each of the unit coils over a grid of target points spanning a target volume, calculating a field per unit current generated by each of the unit coils at each target point, mapping the calculated field per unit current to a target magnetic field, determining optimal coil currents for each of the unit coils, and comparing the magnetic field generated to the target magnetic field.

Preferably, the method of producing the active magnetic shield determines optimal coil currents by minimising the sum of the current values and applying a threshold value defining a maximum value of applied current. The field per unit current is preferably produced by each coil at each magnetic field sensor is calculated using its known target point position. The field per unit current produced by each coil at each magnetic field sensor can be measured by applying a known current to each coil in turn. Preferably, the coil parameters in each of the unit coils are based on unit coil geometry and offset between unit coils.

The method of producing an active magnetic shield preferably further comprises varying the coil parameters in each of the unit coils based on the comparison between the magnetic field generated and the target magnetic field, and repeating the steps of the method until the magnetic field generated and the target magnetic field match.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
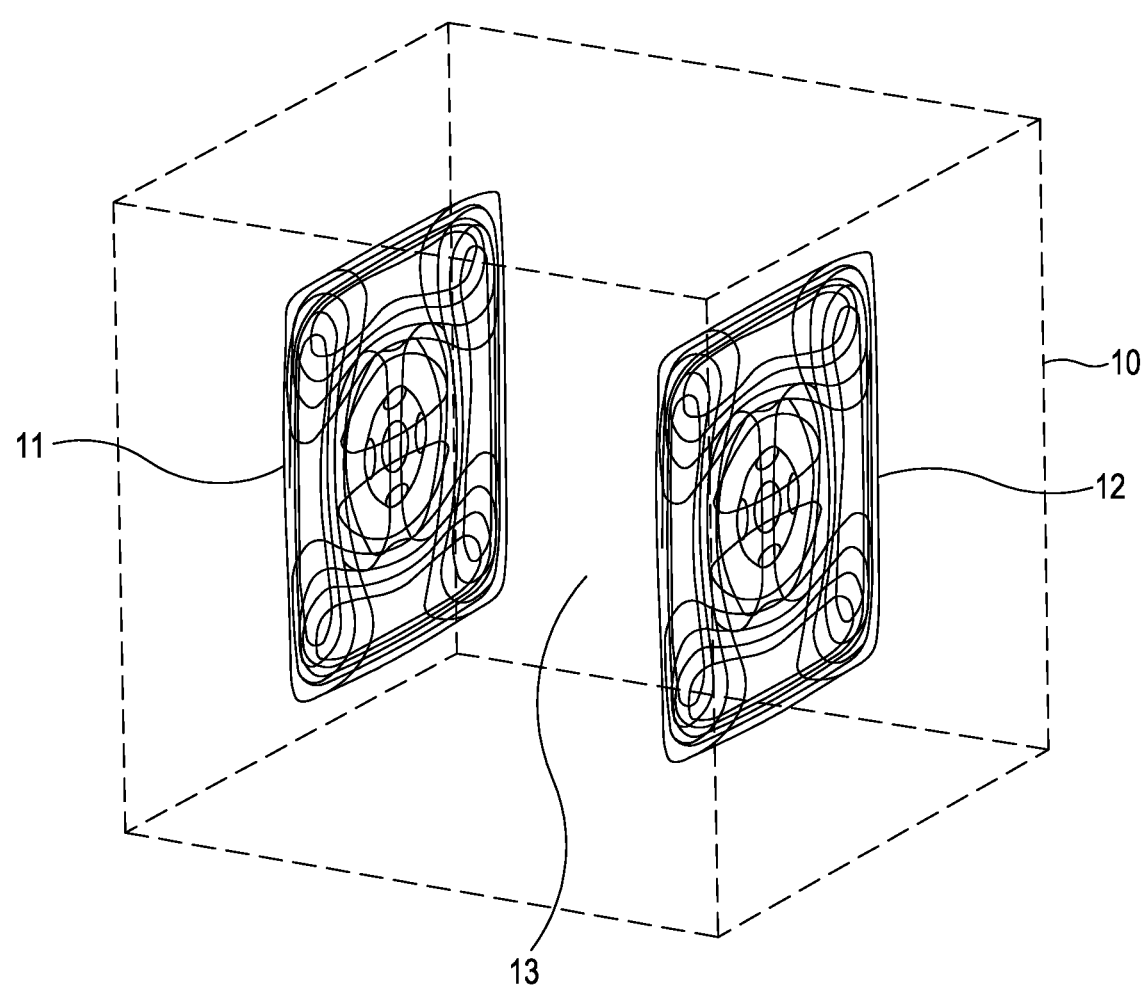
FIG. 1 is an example of a known bi-planar coil system.

FIG. 1 shows a known bi-planar coil system in the context of a magnetically shielded room 10. A first set of coil windings 11 are arranged in a substantially vertical manner on a first side of a volume 13 to be shielded. A second set of coil windings 12 are arranged in a substantially vertical manner on a second side of the volume 13 to be shielded, often referred to as a cancellation volume. The first and second coil windings 11, 12 are restricted to two planes.

Each of the first and second coil windings 11, 12 comprise several layers of intricate wire paths. The layers of wire paths can number three to eight or more. In the present embodiment, the first and second coil windings 11, 12 comprise at least eight layers. The cancellation volume 13 is fixed and limited by the bi-planar arrangement of the coils such that the subject, when enclosed in volume 13 must remain still, producing only small and predictable movements that may be accounted for in the resulting data during processing.

The magnetic fields generated by first and second coil windings 11, 12 interact between one another as well as with the high-permeability materials used in the construction of the magnetically shielded room 10. These interactions distort the produced fields from their expected shapes and change the ratio of produced field strength to applied coil current which adversely effects the efficiency of the shielding. Although these interactions can be incorporated into coil designs, the resulting systems are still limited by the fixed cancellation volume 13 and the tolerable parameters of the subject within the volume 13.

Figure 2A:
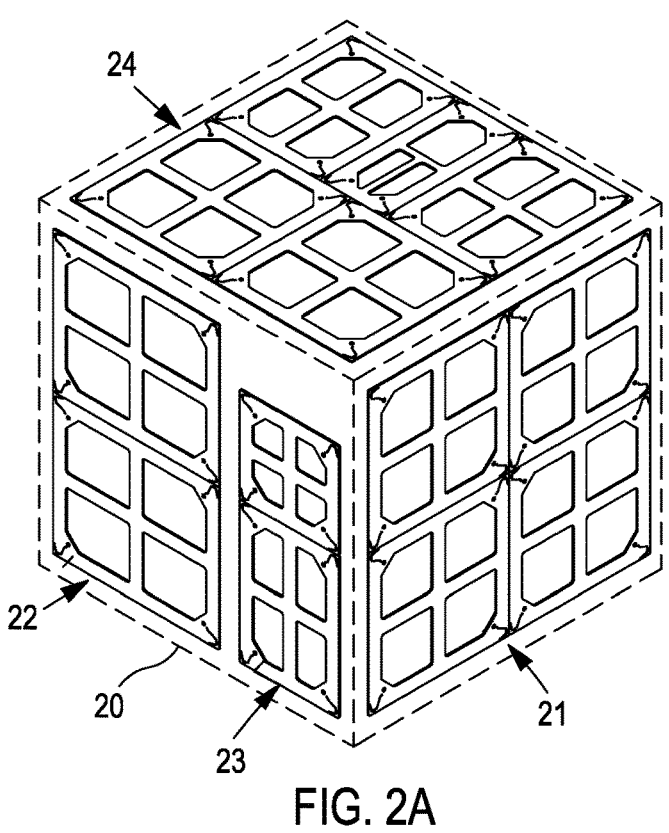
FIG. 2A is a first view of an exemplary active magnetic shield system in accordance with the present invention.

FIG. 2A is a first partial view of an exemplary active magnetic shield arrangement according to the invention. The embodiment shown is that of a "window coil" system in accordance with an embodiment of the present invention.

The active magnetic shielding system comprises an array of magnetic field sensors arranged to detect a local magnetic field. An array of magnetic field elements is provided to generate a magnetic shield, each magnetic field element comprising a plurality of unit coils arranged in a 'window' configuration. The magnetic field elements are distinct and physically displaced from the magnetic field sensors. The unit coils are arranged in at least three planes to negate "blind spots" in the space to be shielded. Where a magnetic shield is generated across a cuboid shaped space, the unit coils are arranged in six planes.

The simple unit coil arrangements comprise wire paths in a variety of geometric shapes, including rectangular, square, and circular wire paths. The coils can be arranged in any shape, and can be chosen to fit the surfaces of the cancellation volume. The wire paths can be placed directly onto the inner surface of walls of the MSR, or embedded therein. An example layout is shown in FIGS. 2A to 9D and an exemplary installed system is shown in FIG. 10.

Although particularly suitable for MSR use, the active magnetic shield arrangement may also be used in isolation.

FIG. 2A shows the arrangement of coils on two of the wall surfaces 21, 22 and on the uppermost ceiling surface 24 of a magnetically shielded room (MSR) 20. The magnetically shielded room 20 is an enclosure with a shell comprising layers of high permeability metals that are good electrical conductors to attenuate spurious magnetic and electrical fields emanating from sources external to the room. The high permeability metals typically comprise mu-metal, forming a passive shield.

The passive shield may comprise a single layer of material with high magnetic permeability, such as mu-metal or another such metal alloy, nickel or otherwise. The passive shield may comprise a further layer of material having a high electrical conductivity, such as copper or aluminium. Alternatively, the passive shield may be constructed of two or more layers of high magnetic permeability and/or high electrical conductivity.

Where the present invention is used in MRI applications, the passive shield may be formed of a material comprising copper, steel or other iron alloy, or aluminium. Such materials contain the fields produced by MRI equipment.

To further reduce the remnant magnetic field in the MSR 20, the passive shielding provided by the mu-metal is complemented by an 'active' shielding system. Active shielding uses electromagnetic coils to produce a magnetic field which is equal and opposite to the magnetic field inside the room, functioning in much the same manner as active noise cancellation technology in headphones to "cancel out" the ambient magnetic field within the cancellation space.

The magnetic field elements are arranged to provide a plurality of unit coils across each surface of an enclosed space. The unit coils are arranged in three planes. The unit coils cooperate to define a cancellation volume. The unit coils can produce a 3-dimensional vector magnetic field pattern that can be adjusted or defined according to preference.

The coil wire path arrangements on wall surface 21 comprise four grids of square coil panels arranged in a 2×2 pattern, each grid having the overall visual appearance of a 'window'. Each of the four grids of wall surface 21 is a coil panel 1 as described in FIGS. 3A-3E.

The coil panels are arranged to cover a significant proportion of the wall surface to which they are mounted. Wall surface 22 has two coil panels 3 as further defined in FIGS. 5A-5D arranged adjacent one another in a substantially vertical 1×2 arrangement. Wall surface 22 has an opening therein for accessing the internal volume 25 of MSR 20. Door surface 23 comprises two coil panels arranged in a substantially vertical 1×2 arrangement so that the combined second wall surface 22 and door surface 23 comprises a 2×2 coil panel arrangement across the wall surface 22. The lowermost portion of door surface 23 comprises coil panel 6 as further described in relation to FIGS. 8A-8D. The uppermost portion of door surface 23 comprises coil panel 5 as further described in relation to FIGS. 7A-7D.

In most known MSR designs, features such as door openings, holes for equipment and removeable panels are 'dead' areas, devoid of shielding as it is not always possible or practical to utilise high permeability metals in such areas, leaving gaps in the passive shield. In the present invention, the active shielding components can be arranged to incorporate room features, such as doors, vents, and other apertures relating to access and functionality of the cancellation volume, into the design process by providing coil panels of appropriate dimensions so as not to obstruct such features. Consequently, surfaces that do not incorporate room features can require fewer coils.

Ceiling surface 24 has an arrangement of five coil panels thereon, extending over substantially the whole of the ceiling surface 24. Two coil panels 1 are arranged adjacent one another such that one coil panel 1 is adjacent uppermost coil panel 3 of wall surface 22 and the other coil panel 1 of ceiling surface 24 is adjacent coil panel 5 of door surface 23 on a first side and an uppermost coil panel 1 of wall surface 21 on a second side. Two further coil panels 2 are arranged at the corners of the quadrilateral ceiling surface 24, with a further coil panel 4 disposed between the coil panels 2 to provide more complete coverage of ceiling surface 24.

The simple geometric coil design makes manufacturing and installation of the arrays easy. The positioning of the coil arrays on the wall, or surface, of the shielded volume or MSR means that the magnetic shielding system does not take up additional space in the shielded volume. The coils are arranged to provide coverage across a central portion of the wall or surface of the shielded volume.

Figure 2B:
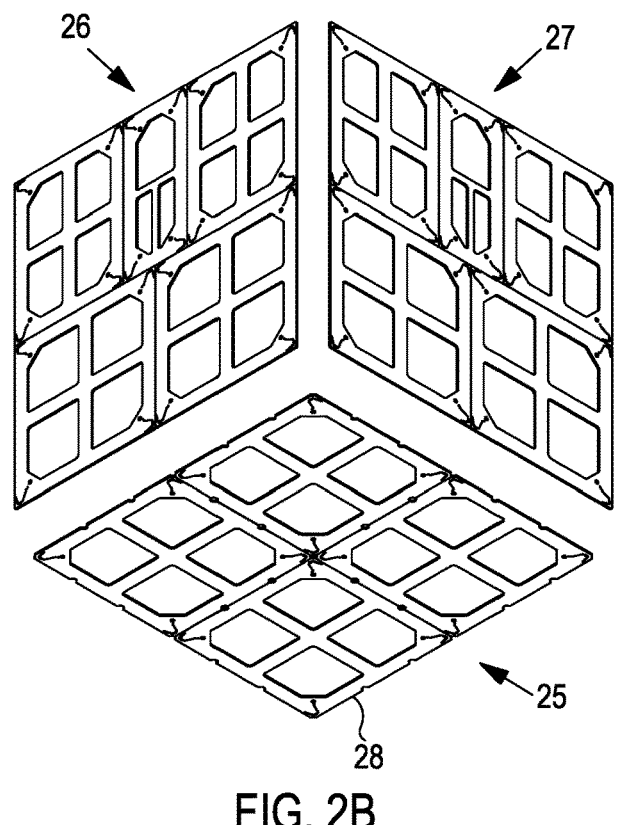
FIG. 2B is a second view of the exemplary active magnetic shield system of FIG. 2A

FIG. 2B is a second partial view of the exemplary active magnetic shield system arranged in a "window coil" configuration of FIG. 2A. When arranged in concert with the features of FIG. 2A, the combined features of FIGS. 2A and 2B form a system that covers all surfaces of the magnetically shielded room 20, defining a single cancellation volume 25.

Floor surface 28 has substantially the same arrangement of window coils as wall surface 21. The window coils are arranged in a 2×2 pattern but formed of four coil panels 7. Coil panel 7 is further described in relation to FIGS. 9A-9D.

Wall surface 26 and wall surface 27 have substantially the same layout of window coils as ceiling surface 24, which is formed of an array of five unit coils to provide even coverage across the respective wall surfaces. Each of wall surfaces 26, 27 have two coil panels 1 arranged adjacent to and horizontal with respect to one another. A coil panel 2 is arranged adjacent coil panel 4 forming a first upper corner of the quadrilateral of wall surface 26, 27. A second coil panel 2 is arranged opposite the coil panel 2 to provide shielding to a second upper corner of the quadrilateral of wall surface 26, 27 opposite the first. Coil panel 4 of wall surfaces 26, 27 is rectangular in shape and arranged such that each of the longer two sides lie adjacent sides of the coil panels 2 it lies between. The lowermost of the two shorter sides lies adjacent coil panels 1 of wall surface 26, 27.

The regular grid pattern of the present embodiment described herein is a simple example, but in practice any number of coil wire paths could be chosen for the array, and a wider range of parameters could be considered. For example, the coils of each magnetic field element could have arbitrary shapes. Different faces of the MSR could feature different coil array layouts, and coils could be allowed to overlap or arranged discretely with respect to one another.

Overlapping the coil wire paths allows partial control of field direction without the need to place coils on all faces.

Figure 2C:
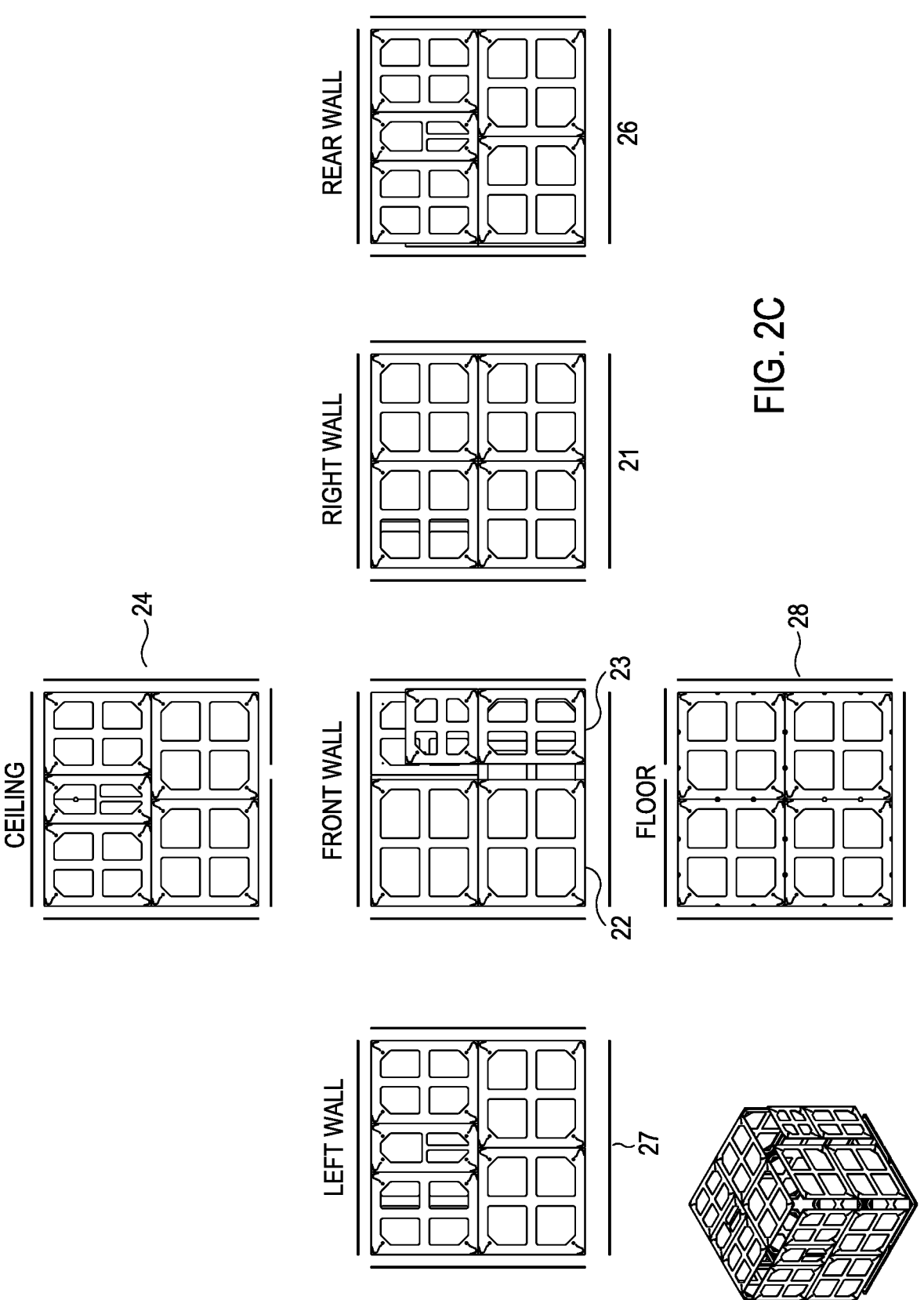
FIG. 2C is a first view of the wall panels of an exemplary active magnetic shield system of FIGS. 2A and 2B.

FIG. 2C shows the plurality of magnetic field elements applied to the surfaces 21, 22, 26, 27, 23, 24, 28 of MSR 20 defining cancellation volume 25. A second planar surface of the coil panels is shown, obscuring the respective coil wire paths of each coil panel. The connection components of the coil wire paths is visible in the corner portions of each of the coil panels.

The system features many coil wire paths, numbering 24 to 48 or more in a typical magnetically shielded room. The number of coil wire paths is determined by the shape of the space shielded, which dictates the number of surfaces to which the unit coils are to be affixed. The present embodiment is therefore tailored to a standard substantially rectangular room for illustrative purposes.

Figure 2D:
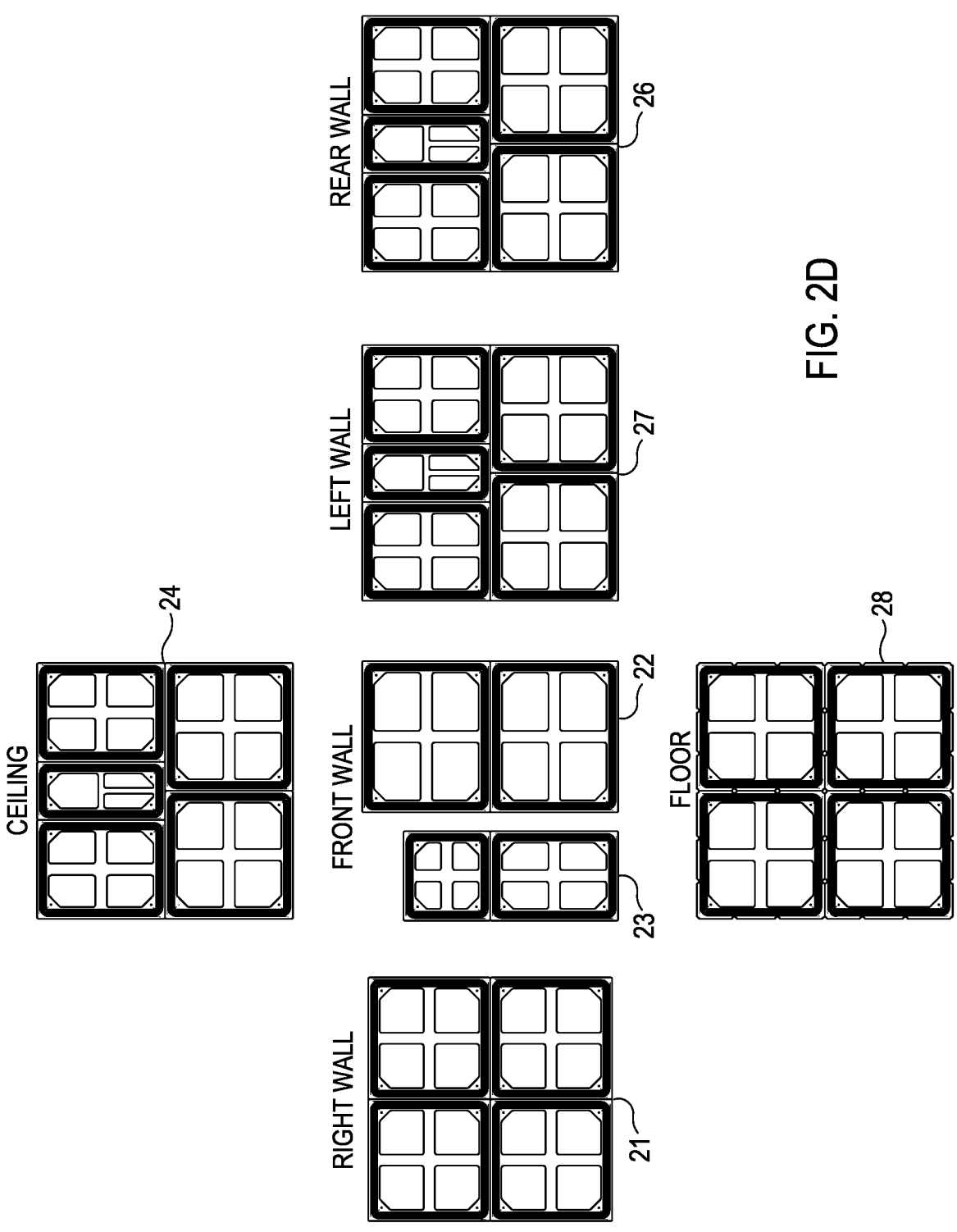
FIG. 2D is a second view of the wall panels of an exemplary active magnetic shield system of FIGS. 2A and 2B.

FIG. 2D shows the unit coils of the magnetic field elements arranged in an array that are obscured in the view of FIG. 2C. Each coil panel type, as shown in FIGS. 2A and 2B, is indicated and the wire paths of each coil panel are visible. Each of the coil panels 1-7 are shown in situ, and are viewed from a first planar side such that the coil wire paths are visible. In the present embodiment, the magnetic field system incorporates multiples of each type of coil panel: ten×coil panel 1, six×coil panel 2, two×coil panel 3, three× coil panel 4, one each of coil panel 5 and coil panel 6, and four×coil panel 7.

Figure 3A:
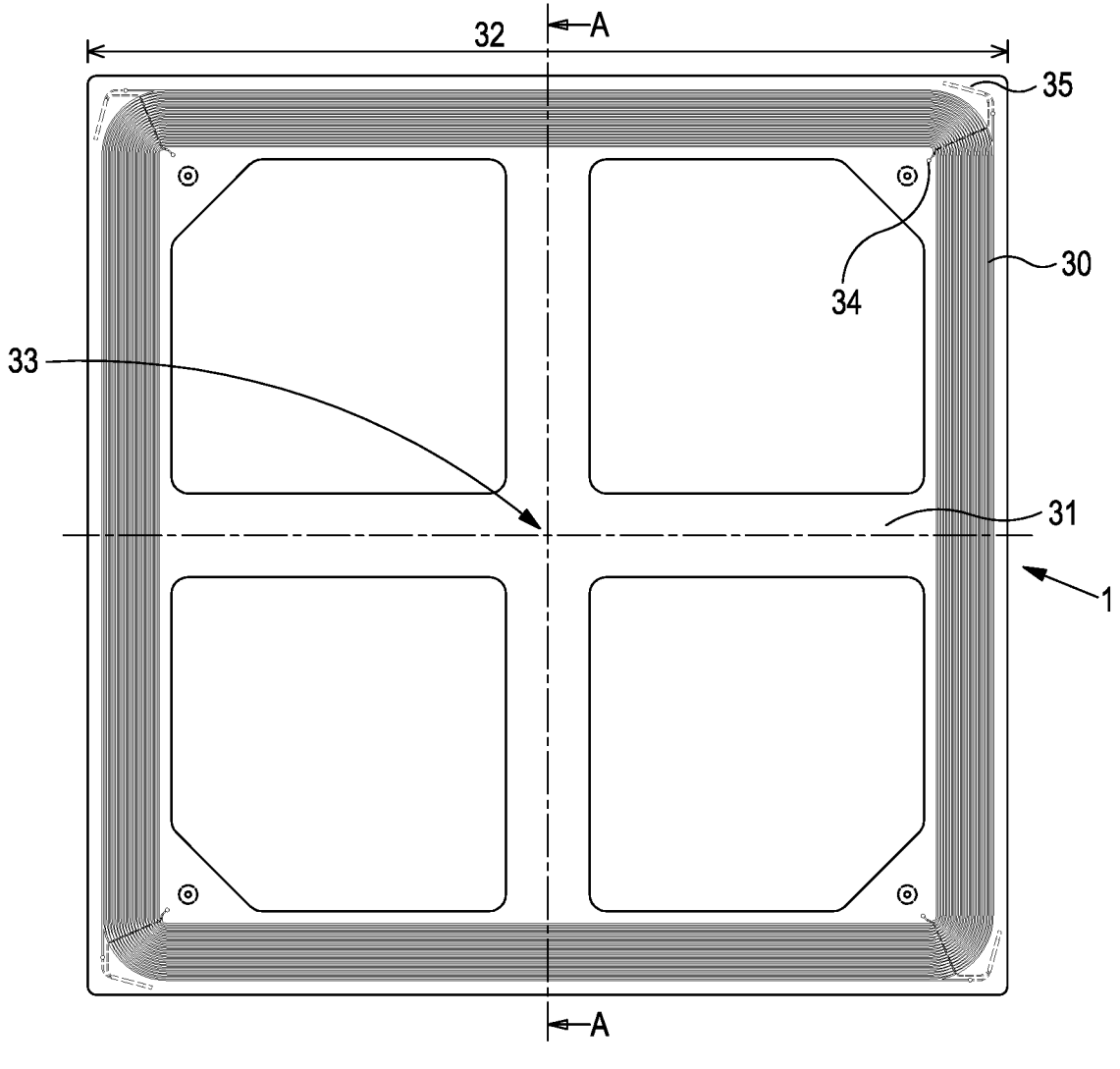
FIG. 3A is a first planar view of a first coil panel in accordance with the invention.

FIG. 3A is a planar view of a first coil panel 1 in accordance with the invention. Coil panel 1 shown as an assembly in planar view. Coil wire path 30 is affixed to a first planar surface of supporting panel 31. Coil wire path 30 extends around the periphery of the planar surface of supporting panel 31 in a square shape to fit within the surface area of the panel, which is also a regular quadrilateral in the present embodiment. The coil wire path 30 extends along each panel side length 32, which are substantially equal. The coil wire path 30 is a continuous winding formed or either a discrete piece or several pieces joined to form a singular wire that is repeatedly wound to form a coil of adjacent sections.

When placed in situ on the selected surface of MSR 20, coil panel 1 is mounted such that wire paths 30 are adjacent the surfaces of MSR 20 and obscured by panel 31 when viewed from the cancellation volume 25. In some embodiments the wire paths 30 are embedded in surfaces of the MSR 20. However, coil panel 1 may also be arranged with the wire paths 30 exposed and facing the cancellation volume 25.

Certain coil parameters are determined, which in the present embodiment are the symmetrical side lengths 32 of each coil square 30, a regular spacing between coil centres 33, and the distance of the centre of the 2×2 grid from the centre of each surface of the MSR. For a given set of coil parameters, the magnetic field generated by a unit of applied current in each coil over a regular grid of 'target points' spanning a volume of interest is calculated. The magnetic field calculation may incorporate data relating to interactions with the nearby mu-metal of the surfaces of the MSR 20, where relevant or desirable.

Each target point is determined according to user preference. In a preferred arrangement, a cancellation volume is defined by the arrangement of the sensor array and the area of coverage. These parameters are used to determine an approximate cubic cancellation volume that is mapped with a grid of target points. The number of target points is determined according to desired resolution. In a preferred embodiment, target points can be set at 5 cm intervals throughout the cubic cancellation volume.

The calculated field per unit current generated at the target points is then mapped to a target magnetic field by identifying optimal coil currents. The target magnetic field can be selected as a magnetic field which has the same value at each target point, known as a 'uniform field'. Alternatively, the target magnetic field can be a magnetic field that varies linearly with position, known as a 'field gradient'. Some embodiments of the invention use at least one uniform target magnetic field, and other embodiments use at least one field gradient target magnetic field. Further embodiments may use a mixture of a uniform target magnetic field and a field gradient target magnetic field, or any number of each in combination.

Figures 3B, 3C:
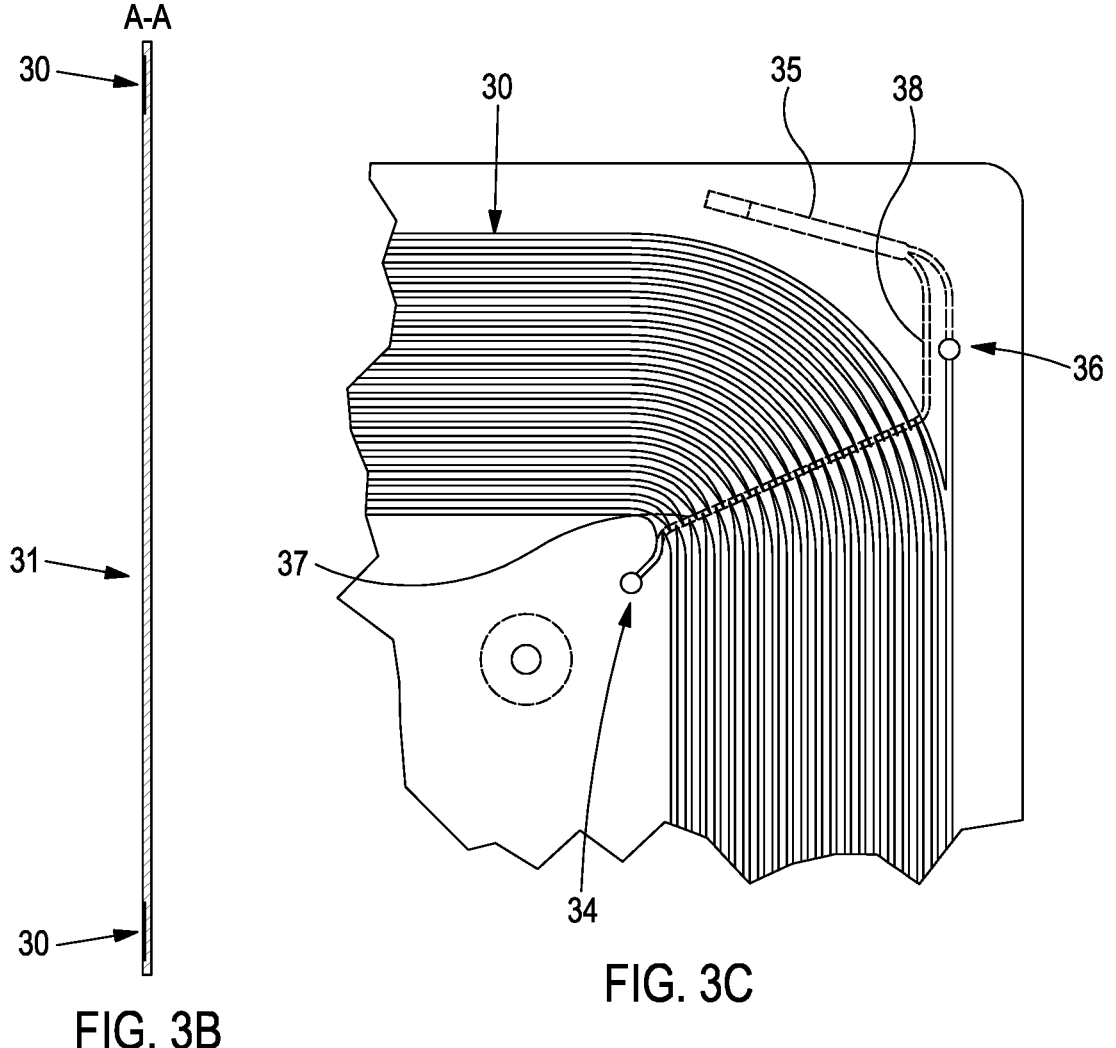
FIG. 3B is a section view of the first coil panel of FIG. 3A.
FIG. 3C is a cut away section view of the coils of the first coil panel of FIG. 3A.

FIG. 3B is a section view of the first coil panel 1 of FIG. 3A. Coil wire path 30 is shown as recessed into the planar surface of supporting panel 31. Supporting panel 31 is formed of any suitable non-metallic and/or non-magnetic material. However, in some embodiments, the supporting panel may be formed of an appropriate material such that the supporting panel provides passive shielding.

The unit coil windings of coil wire path 30 are typically recessed to a depth of 3 mm, and remain visible on the first planar surface of supporting panel 31. Each successive winding is offset from the previous winding by 2 mm, with each of the wires of wire path 30 being typically 1.5 mm diameter.

The surface of supporting panel 31 may, in some embodiments, be covered to protect or to simply obscure the unit coil.

FIG. 3C is a cut away section view of the coil wire path 30 of the first coil panel 1 of FIG. 3A, showing the coil wire path 30 and associated connections. The coil wire path 30 is formed of a single winding arranged around the periphery of the planar surface of supporting panel 31 such that that each successive winding is adjacent the previous iteration.

The coil wire path 30 of the present embodiment is formed of 20 windings extending between coil terminal 34 and coil terminal 36. The magnetic field strength scales linearly with B~NI, where I is current and N is the number of windings. In the present embodiment, N=20 is selected to produce sufficient field.

Based on the known maximum current of the current source and an estimate of the magnetic field inside the MSR, N can be chosen to ensure that sufficient field is generated by the system to produce magnetic field of required strength.

A coil bridging section 37 extends between coil terminal 34 and coil terminal 36. An external connector 35 connects both coil terminal 36 and coil bridging section 37 to an external current source, the latter being connected via coil bridging connector 38.

The external current source is arranged to provide a set of current values such that the coils of each coil wire path produce arbitrary vector magnetic field patterns in accordance with the current applied to each of the unit coils. The magnetic field patterns are not limited to a field in the x, y, or z direction; therefore a subject of measurement may be placed in any location within the shielded cancellation volume.

The external current source is arranged to apply a variety of current values to the unit coils to vary the magnetic field patterns produced based on a range of criteria. The magnetic field patterns may be updated to better attenuate the local magnetic field, based on magnetic field sensor measurements or other data relevant to changes in external interference. The magnetic field patterns may also be dynamically updated to track a moving subject within the cancellation space.

The current values may be determined by feedback algorithm, or via pre-determined or measured values. The current calculation method can be arranged to compensate for interactions between the magnetic field elements and passive shielding, where passive shielding is used.

Figure 3D:
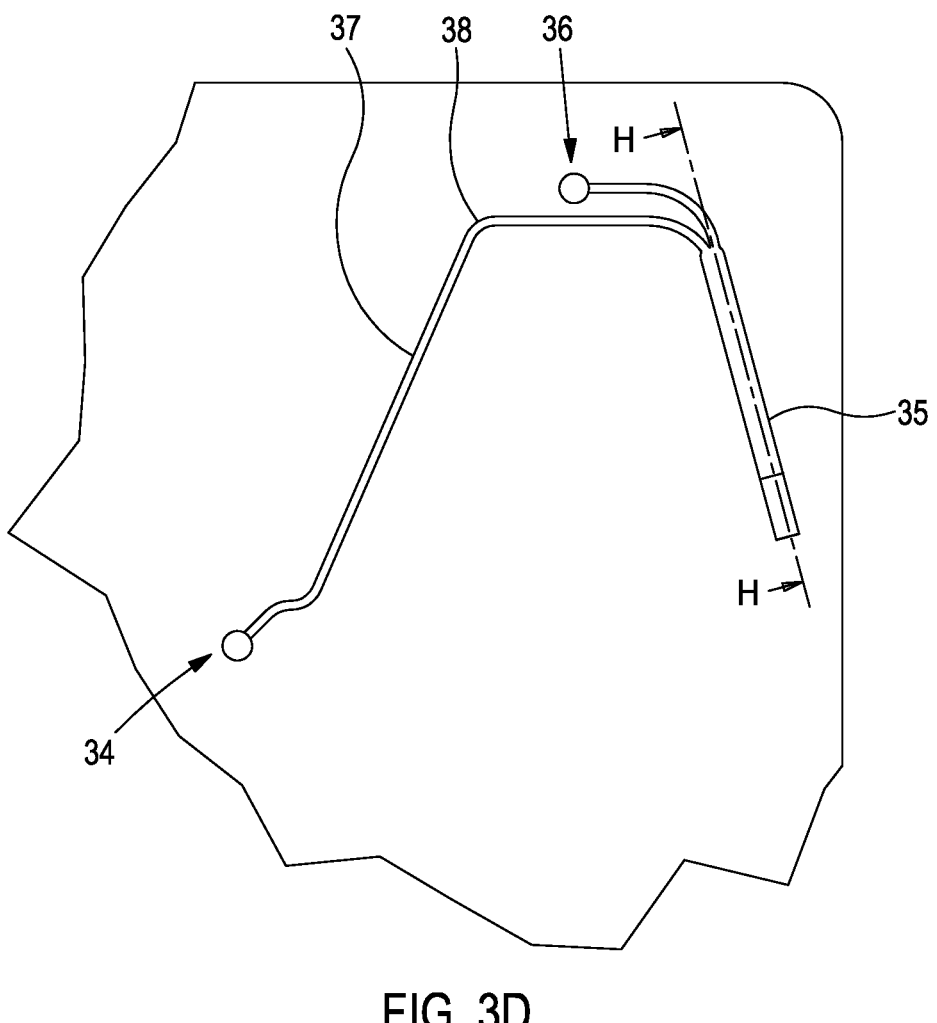
FIG. 3D is a second planar view of the coil connections of the first coil panel of FIG. 3A

FIG. 3D is a second planar view of the coil connections of the first coil panel 1 of FIG. 3C. The coil terminals 34, 36, coil bridging section 37, coil bridging connector 38 and external connector 35 are located on a second planar face of the supporting panel 31 opposite the first. The coil wire path 30 is located on the first planar surface such that only the components located on the second planar face of supporting panel 31 are visible and/or accessible. In embodiments in which the coil wire path 30 is on a planar face of supporting panel 31 visible from inside the cancellation volume 25 of magnetically shielded room 20, the coil terminals 34, 36, coil bridging section 37, coil bridging connector 38 and external connector 35 are located on the same planar face as that of the coil wire path 30.

Figure 3E:
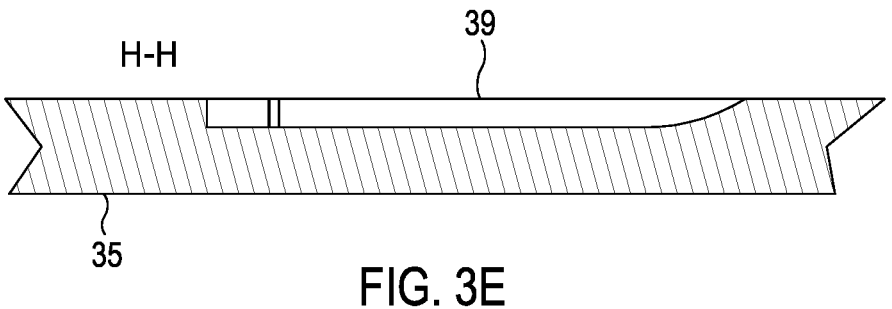
FIG. 3E is a section view of the coil connection of FIG. 3D.

FIG. 3E is a section view of external connector 35 showing recess 39 formed by standard manufacturing processes. The recess may be present to accommodate coil wire path 30 where a flush panel surface profile is preferred. The connector recess 39 ensures that the returning wire of the coil is flush to the surface of the panel for ease of mounting during installation.

Figure 4A:
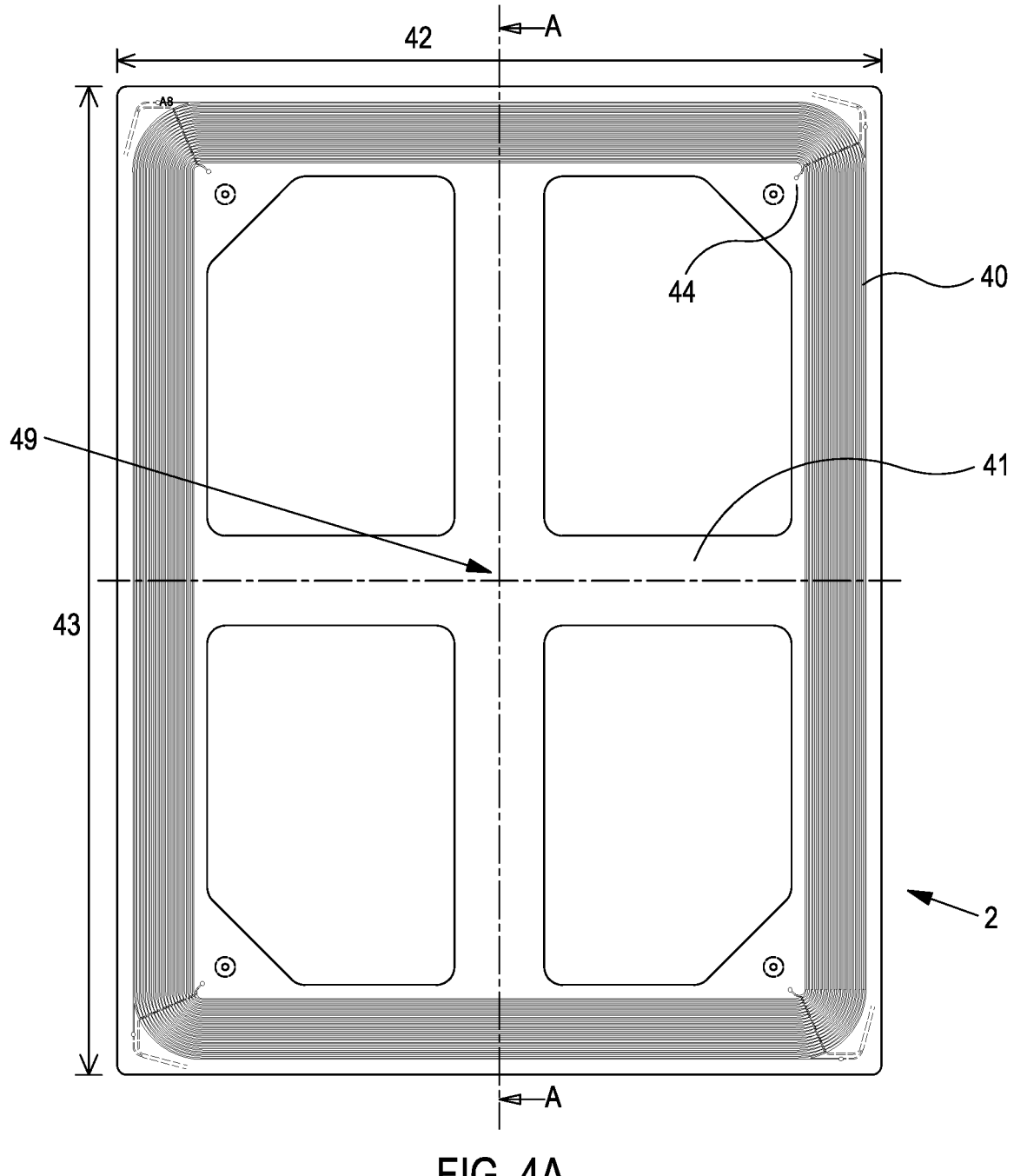
FIG. 4A is a planar view of a second coil panel in accordance with the invention.

FIG. 4A is a planar view of a second coil panel 2 in accordance with the invention. Coil panel 2 shown as an assembly in planar view. Coil wire path 40 is affixed to a first planar surface of supporting panel 41. Coil wire path 40 extends adjacent the periphery of the planar surface of supporting panel 41 in a rectangular shape to fit within the surface area of the panel, which is also rectangular in the present embodiment. The supporting panel 41 has a panel side width 42 that is shorter in length than panel side length 43. Consequently, the section of the coil wire path 40 that extends adjacent panel side length 43 extends over a greater length than the section of the coil wire path 40 that extends adjacent panel side width 42.

The coil wire path 40 extends along a first panel side width 42, a first panel side length 43, a second panel side width 42, and a second panel side length 43 to form a rectangular footprint. The coil wire path 40 is a continuous winding formed or either a discrete piece or several pieces joined to form a singular wire that is repeatedly wound to form a coil of adjacent sections in a selected number of iterations.

When placed in situ on the selected surface of MSR 20, coil panel 2 is mounted such that wire path 40 is adjacent the surfaces of MSR 20 and obscured by panel 41 when viewed from the cancellation volume 25. In some embodiments the wire paths 40 are embedded in surfaces of the MSR 20. However, coil panel 2 may also be arranged with the wire paths 40 exposed and facing the cancellation volume 25.

The relevant coil parameters are determined, which in the present embodiment are the side width 42 and side length 43 of each coil wire path 40, regular spacing between coil centre 49 and centres of adjacent coils, and the distance of the centre of the 2×2 grid from the centre of each surface of the MSR 20.

In a preferred embodiment, coil parameters are determined by assuming the cancellation volume is a cube with no "holes" or non-shielded areas in a passive shield. An arrangement of four coils is applied to each surface. The side length, the offset from the centre, and the height of the arrangement are varied, the quality of the solution for each component is recorded. The quality of the solution is derived from the square root of the sum of the squared differences between the desired magnetic field at each target point and the magnetic field produced by the coil parameters at each target point. If the coil perfectly reproduces the desired field the quality of the solution is zero.

The quality data is combined to determine a single quality factor for each surface. The parameters required for each surface are co-optimised such that they are calculated simultaneously, rather than on a face per face basis. In this manner, the vector magnetic field pattern is optimised.

For a given set of coil parameters, the magnetic field generated by a unit of applied current in each coil over a regular grid of 'target points' spanning the cancellation volume 25 is calculated. Where relevant, the magnetic field calculation may incorporate data relating to interactions with the nearby mu-metal of the surfaces of the MSR 20.

In most aspects, coil panel 2 is substantially the same as coil panel 1 in form, construction, and materials. Likewise coil panels 3, 4, 5, 6 and 7. The description of coil panel 1 is therefore applicable to all coil panels of the present embodiment, save for where the description of an individual panel indicates otherwise.

Figures 4B, 4C:
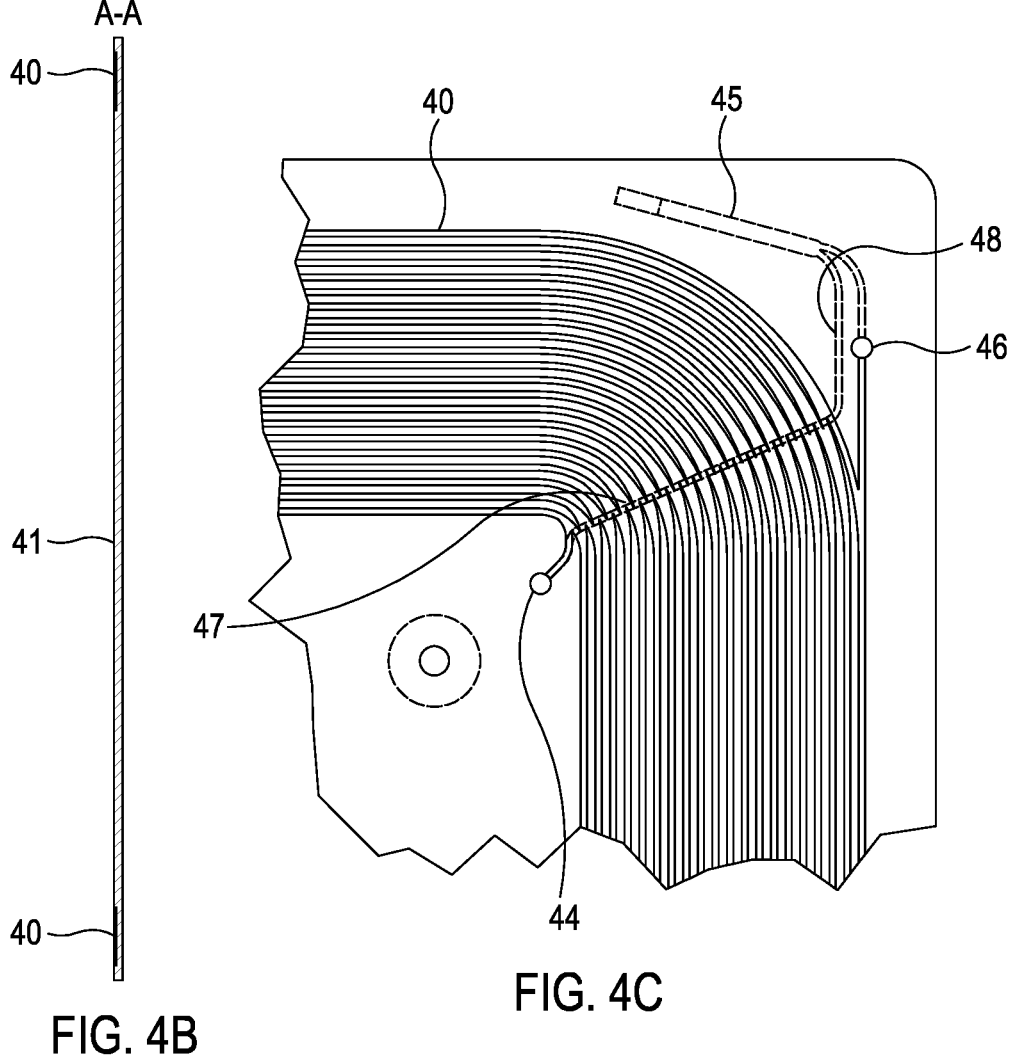
FIG. 4B is a section view of the second coil panel of FIG. 4A.
FIG. 4C is a cut away section view of an arrangement of coils of the second coil panel of FIG. 4A.

FIG. 4B is a section view of the second coil panel of FIG. 4A, in which supporting panel 41 is shown in cross section. Coil wire path 40 is shown as recessed into the planar surface of supporting panel 41. The windings of coil wire path 40 are typically recessed into the surface of supporting panel 41 and remain visible on its first planar surface. Each successive winding is offset from the previous in a coil comprising a single layer of windings.

FIG. 4C is a cut away section view of the coil wire path 40 of the second coil panel 2 of FIG. 4A showing the coil wire path 40 and associated connections. The coil wire path 40 is formed of a single winding arranged around the periphery of the planar surface of supporting panel 41 such that that each successive winding is adjacent the previous. The coil wire path 40 of the present embodiment is formed of 20 windings extending between coil terminal 44 and coil terminal 46.

A coil bridging section 47 extends between coil terminal 44 and coil terminal 46. An external connector 45 connects both coil terminal 46 and coil bridging section 47 to an external current source. The coil bridging section 47 is connected to the external connector 45 via coil bridging connector 48.

Figure 4D:
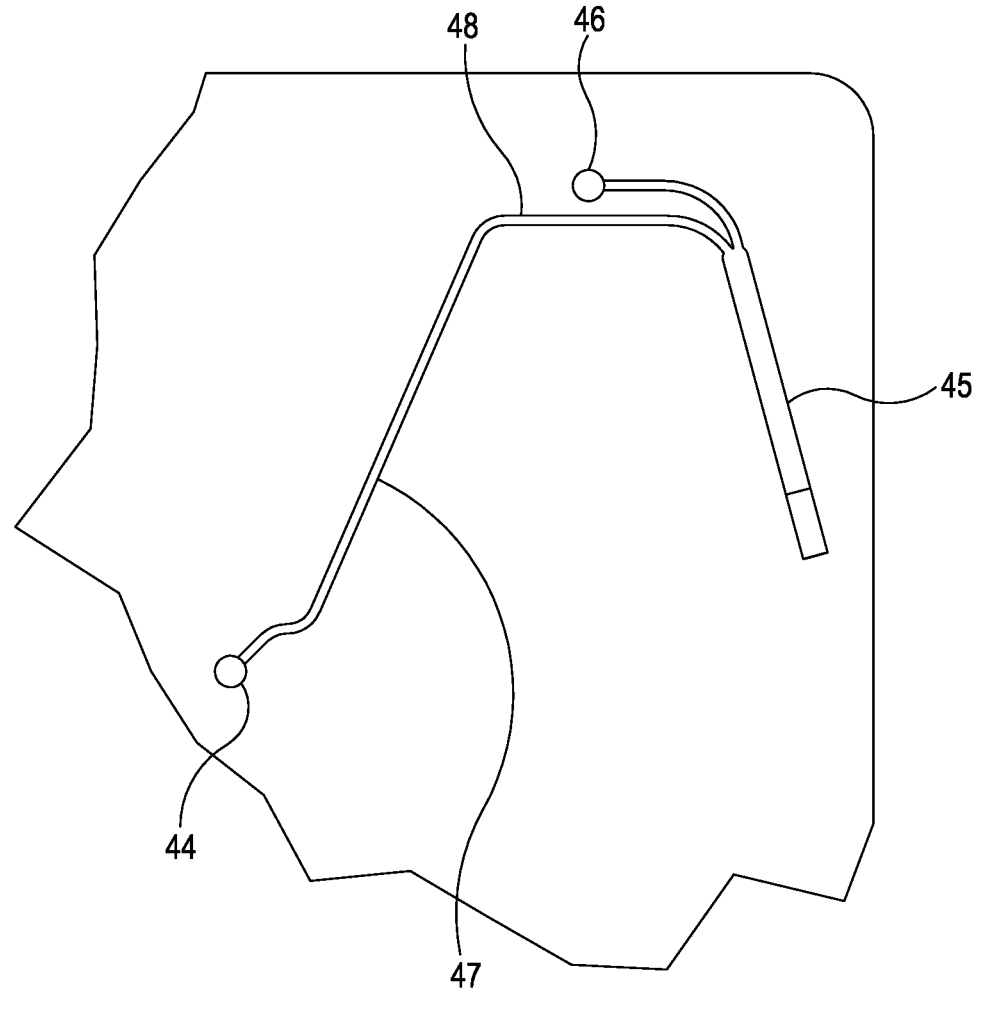
FIG. 4D is a cut away section view of the coil connections of the second coil panel of FIG. 4A.

FIG. 4D is a second planar view of the coil connections of the second coil panel 2 of FIG. 4C. The coil terminals 44, 46, coil bridging section 47, coil bridging connector 48 and external connector 45 are located on a second planar face of the supporting panel 41 opposite the first. The coil wire path 40 is located on the first planar surface such that only the components located on the second planar face of supporting panel 41 are visible and/or accessible.

Figure 5A:
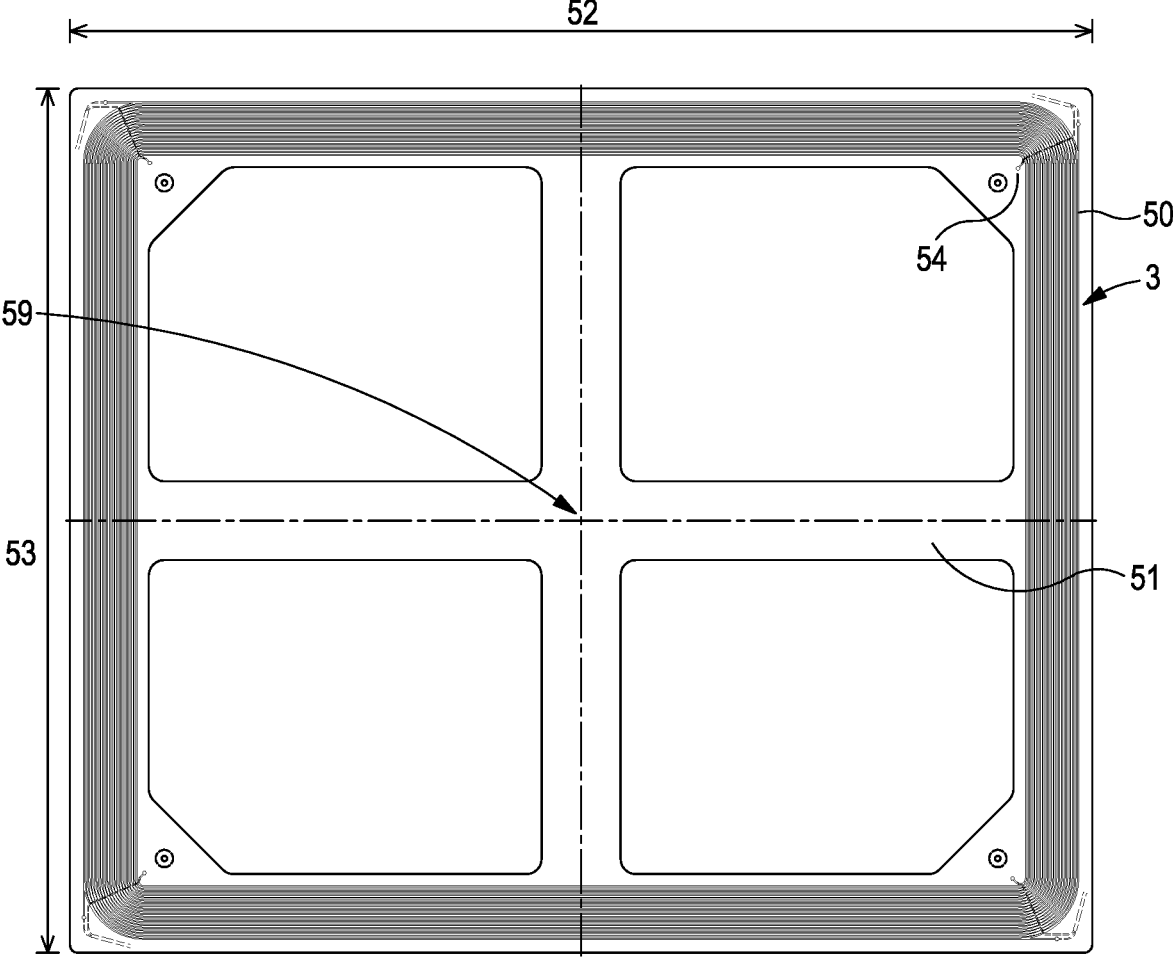
FIG. 5A is a planar view of a third coil panel in accordance with the invention.

FIG. 5A is a planar view of a third coil panel 3 in accordance with the invention. Coil panel 3 shown as an assembly in planar view. Coil wire path 50 is affixed to a first planar surface of supporting panel 51. Coil wire path 50 extends adjacent the periphery of the planar surface of supporting panel 51 in a rectangular shape to fit within the surface area of the panel, which is also rectangular in the present embodiment. The supporting panel 51 has a panel side width 52 that is longer in length than panel side length 53. Consequently, the section of the coil wire path 50 that extends adjacent panel side width 52 extends over a greater length than the section of the coil wire path 50 that extends adjacent panel side length 53.

The coil wire path 50 extends along a first panel side width 52, a first panel side length 53, a second panel side width 52, and a second panel side length 53 to form a rectangular footprint. The coil wire path 50 is a continuous winding formed or either a discrete piece or several pieces joined to form a singular wire that is repeatedly wound to form a coil of adjacent sections.

The relevant coil parameters are determined, which in the present embodiment are the side width 52 and side length 53 of each coil wire path 50, regular spacing between coil centre 59 and centres of adjacent coils, and the distance of the centre of the 2×2 grid from the centre of each surface of the MSR 20.

In the same manner as coil panels 1, 2, 3, 5, 6 and 7, supporting panel 51 has cut outs in the central portion of the coil panel 51 defined peripherally by coil wire path 50. Four cut out sections are arranged symmetrically in a 2×2 pattern such that the material of the central portion of supporting panel 51 is arranged in a cross shape to provide rigidity while also providing access to underlying features, for example, a small access hole, or bolts in the mu-metal panels. Alternatively, each coil wire path 50 can be mounted on a solid square. The horizontal component of the cross shape is substantially parallel to panel side width 52 and the vertical component is substantially parallel to panel side length 53. Coil centre 59 is located at the intersection of the horizontal and vertical components of the supporting panel 51 material in the central portion. Both the horizontal and vertical components of the central portion of supporting panel 51 are of equal width and depth.

Figures 5B, 5C:
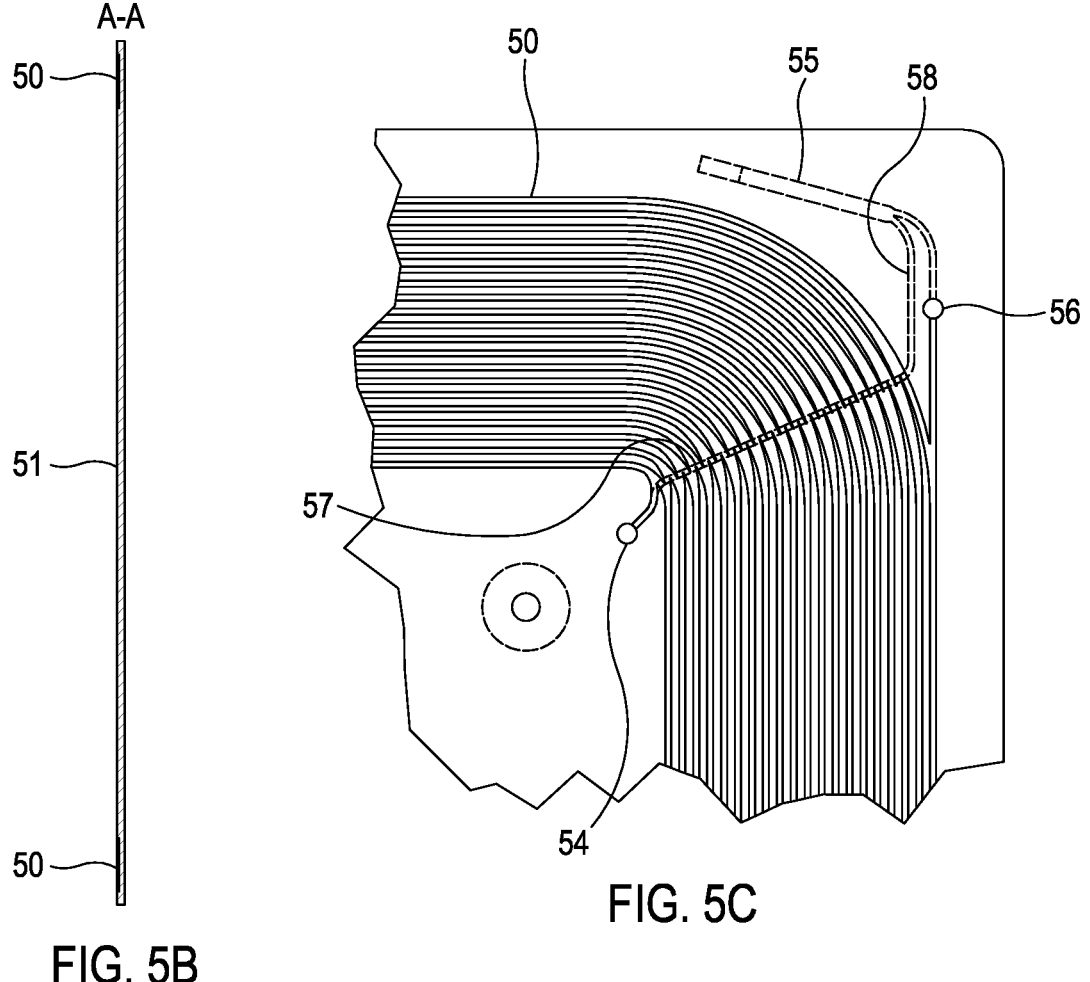
FIG. 5B is a section view of the third coil panel of FIG. 5A.
FIG. 5C is a cut away section view of an arrangement of coils of the third coil panel of FIG. 5A.

FIG. 5B is a section view of the second coil panel of FIG. 5A, in which supporting panel 51 is shown in cross section. Coil wire path 50 is shown as recessed into the planar surface of supporting panel 51. The windings of coil wire path 50 are typically recessed into the surface of supporting panel 51 and remain visible on its first planar surface.

FIG. 5C is a cut away section view of the coil wire path 50 of the third coil panel 3 of FIG. 5A showing the coil wire path 50 and associated connections. The coil wire path 50 is formed of a single winding arranged around the periphery of the planar surface of supporting panel 51 such that that each successive winding is adjacent the previous. The coil wire path 50 of the present embodiment is formed of 20 windings extending between coil terminal 54 and coil terminal 56.

Figure 5D:
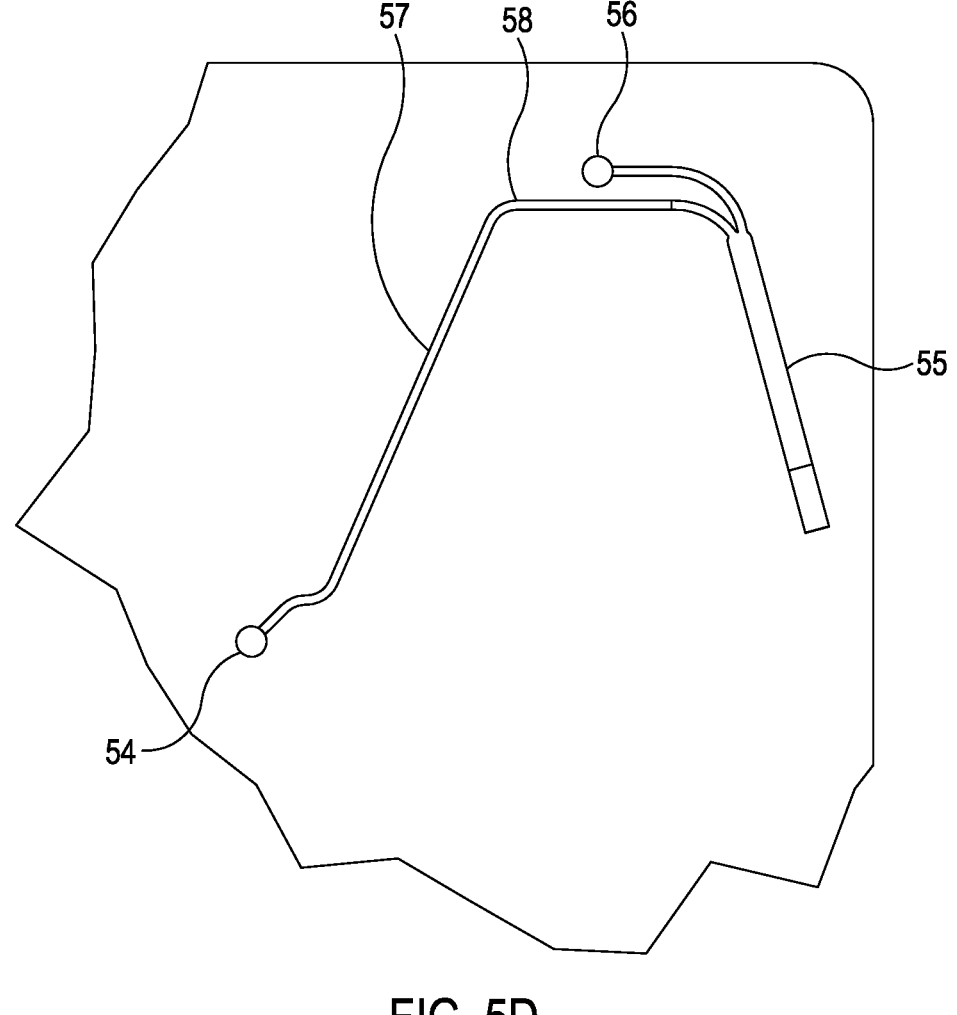
FIG. 5D is a cut away section view of the coil connections of the third coil panel of FIG. 5A.

FIG. 5D is a second planar view of the coil connections of the third coil panel 3 of FIG. 5C. The coil terminals 54, 56, coil bridging section 57, coil bridging connector 58 and external connector 55 are located on a second planar face of the supporting panel 51 opposite the first. The coil wire path 50 is located on the first planar surface such that only the components located on the second planar face of supporting panel 51 are visible and/or accessible.

Figures 6A, 6B:
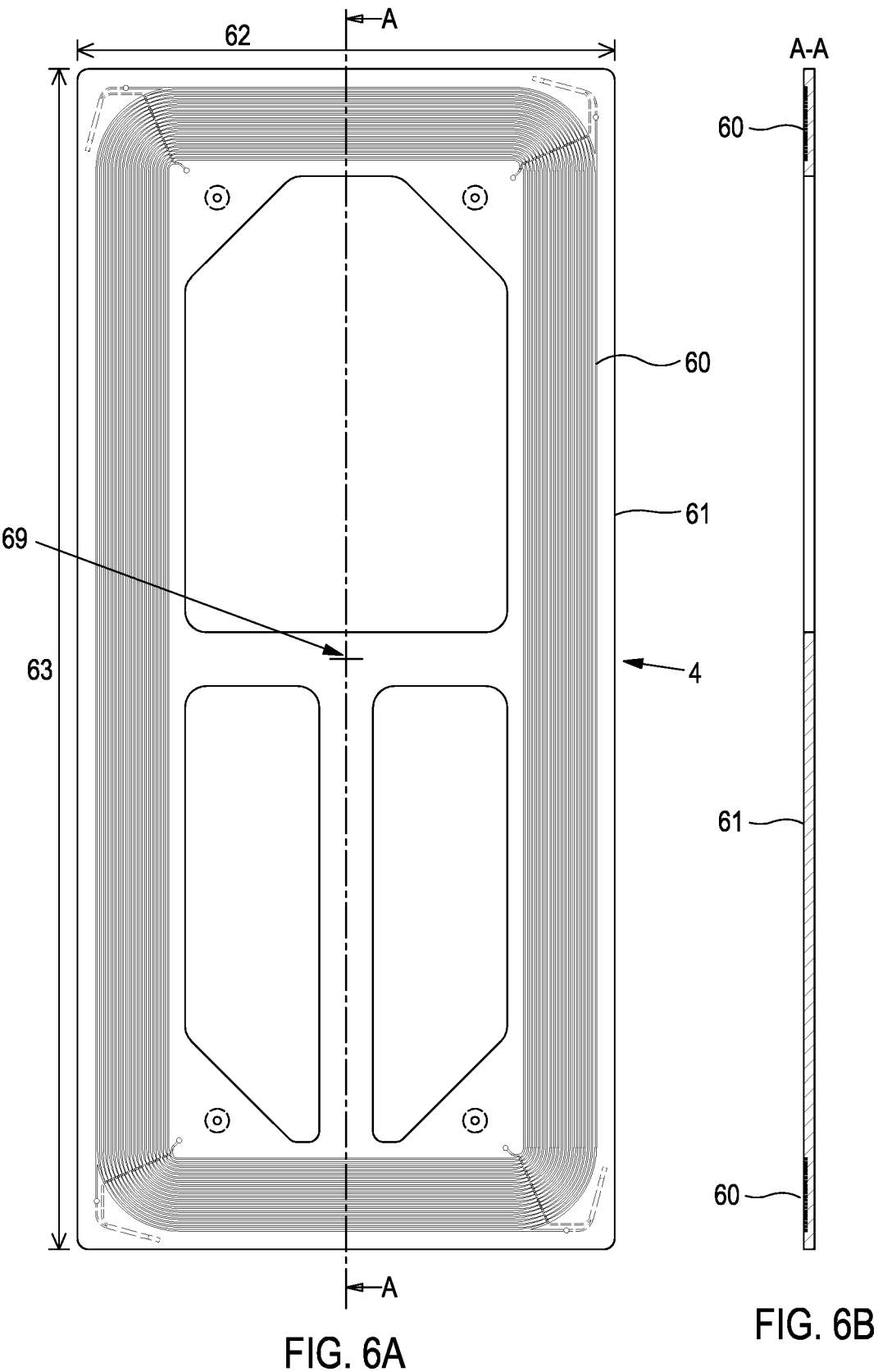
FIG. 6A is a planar view of a fourth coil panel in accordance with the invention.
FIG. 6B is a section view of the fourth coil panel of FIG. 6A.

FIG. 6A is a planar view of a fourth coil panel 4 in accordance with the invention. Coil panel 4 is shown as an assembly in planar view. Coil wire path 60 is affixed to a first planar surface of supporting panel 61. Coil wire path 60 extends adjacent the periphery of the planar surface of supporting panel 61 in a rectangular shape to fit within the surface area of the panel, which is also rectangular in the present embodiment. The supporting panel 61 has a panel side width 62 that is shorter in length than panel side length 63. Consequently, the section of the coil wire path 60 that extends adjacent panel side length 63 extends over a greater length than the section of the coil wire path 60 that extends adjacent panel side width 62.

The supporting panel 61 comprises three cut out sections within the central portion of the supporting panel 61 defined by the coil wire path 60. A first central piece of supporting panel 61 extends between panel side lengths 63 such that coil centre 69 falls within the central piece of supporting panel 61. A second central piece of supporting panel 61 extends from one of the panel side widths 62 to the first central piece to form a t-shaped member. The first and second central pieces of the supporting panel 61 have substantially the same width as one another. The supporting panel 61 has a consistent cross sectional area.

When placed in situ on the selected surface of MSR 20, coil panel 4 is mounted such that wire path 60 is adjacent the surfaces of MSR 20 and obscured by panel 61 when viewed from the cancellation volume 25. In some embodiments the wire paths 60 are embedded in surfaces of the MSR 20. However, coil panel 4 may also be arranged with the wire paths 60 exposed and facing the cancellation volume 25.

FIG. 6B is a section view of the fourth coil panel 4 of FIG. 6A, in which supporting panel 61 is shown in cross section. Coil wire path 60 is shown as recessed into the planar surface of supporting panel 61. The windings of coil wire path 60 are typically recessed into the surface of supporting panel 61.

Figure 6C:
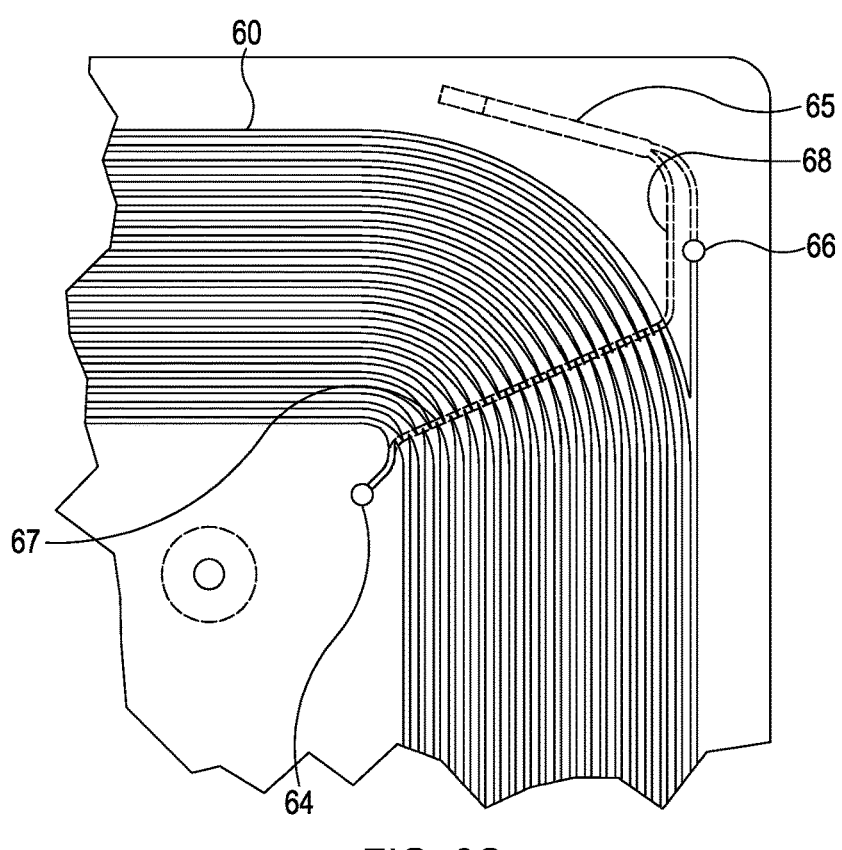
FIG. 6C is a cut away section view of an arrangement of coils of the fourth coil panel of FIG. 6A.

FIG. 6C is a cut away section view of the coil wire path 60 of the fourth coil panel 4 of FIG. 6A showing the coil wire path 60 and associated connections. The coil wire path 60 is formed of a single winding arranged around the periphery of the planar surface of supporting panel 61 such that that each successive winding is positioned adjacent the previous. The coil wire path 60 of the present embodiment is formed of 20 windings extending between coil terminal 64 and coil terminal 66.

Figure 6D:
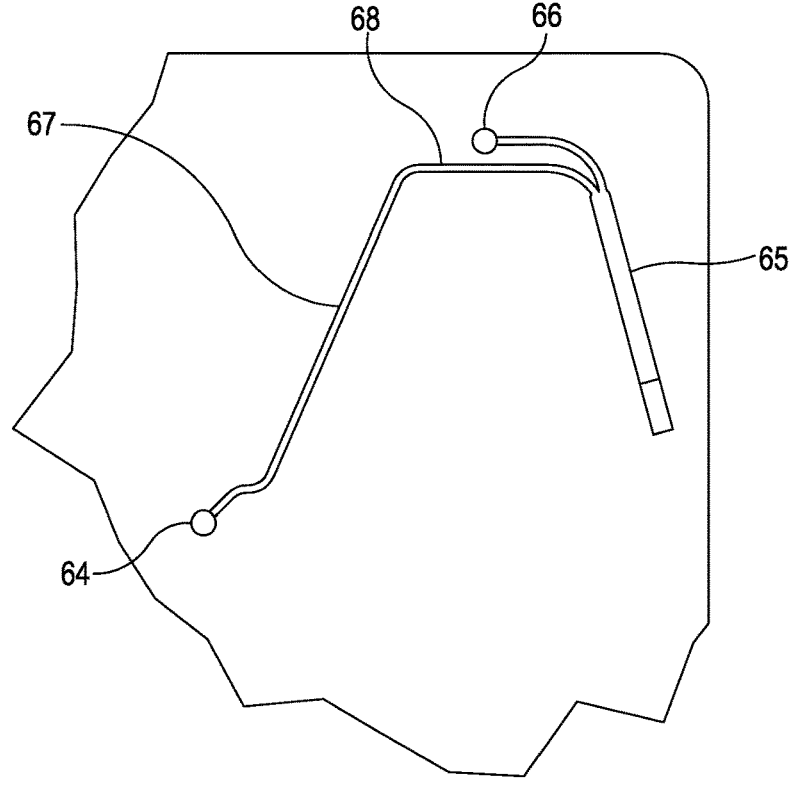
FIG. 6D is a cut away section view of the coil connections of the fourth coil panel of FIG. 6A.

FIG. 6D is a second planar view of the coil connections of the fourth coil panel 4 of FIG. 6C. The coil terminals 64, 66, coil bridging section 67, coil bridging connector 68 and external connector 65 are located on a second planar face of the supporting panel 61 opposite the first. The coil wire path

60 is located on the first planar surface such that only the components located on the second planar face of supporting panel 61 are visible and/or accessible.

Figure 7A:
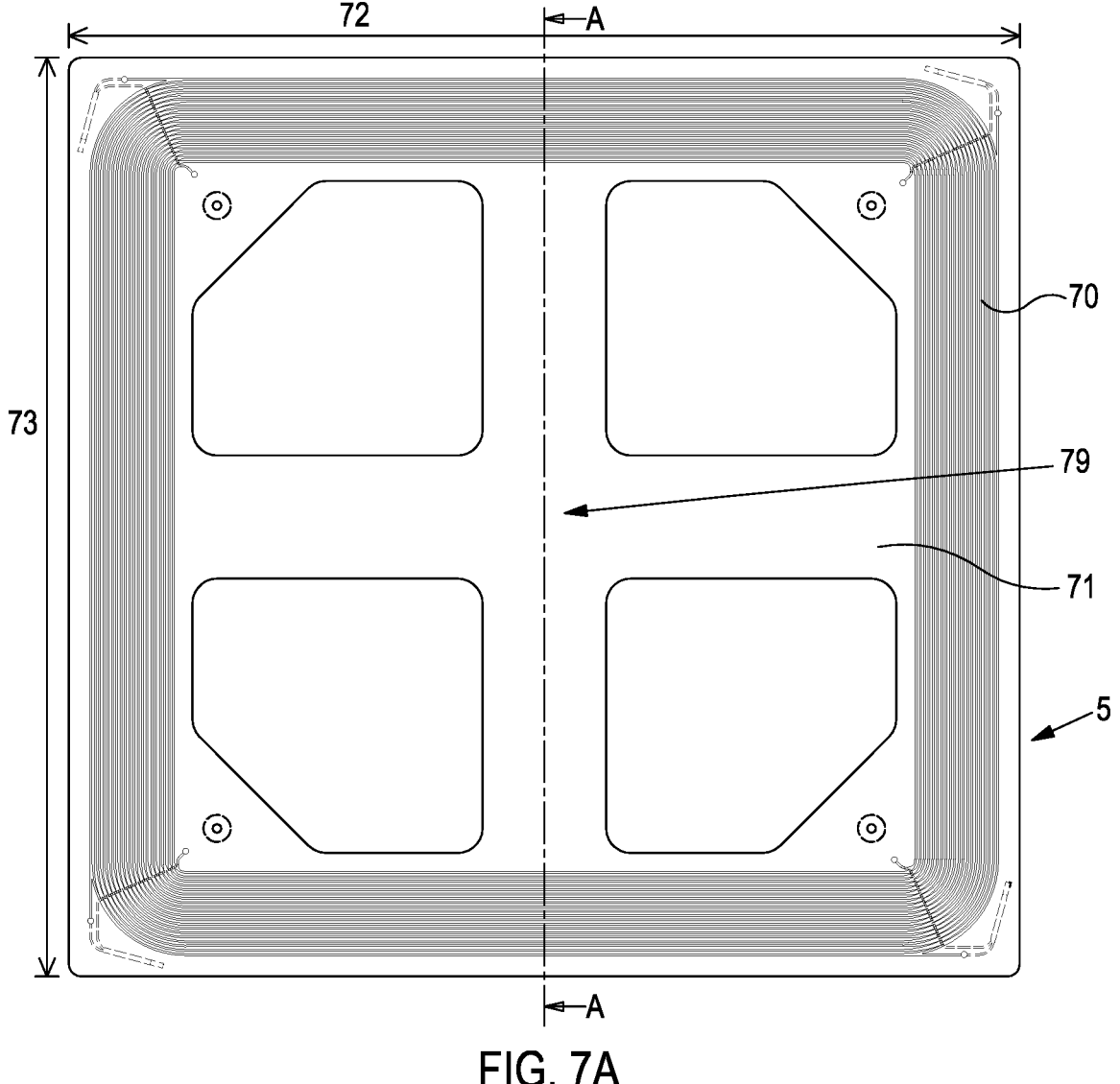
FIG. 7A is a planar view of a fifth coil panel in accordance with the invention.

FIG. 7A is a planar view of a fifth coil panel 5 in accordance with the invention. Coil panel 5 is shown in planar view. Coil wire path 70 is affixed to a first planar surface of supporting panel 71. Coil wire path 70 extends around the periphery of the planar surface of supporting panel 71 in a square shape to fit within the surface area of the panel, which is also a regular quadrilateral in the present embodiment. The coil wire path 70 extends along each panel side length 72, 73 which are substantially equal. The coil wire path 70 is a continuous winding formed or either a discrete piece or several pieces joined to form a singular wire that is repeatedly wound to form a coil of adjacent sections.

Coil panel 5 is arranged such that wire paths 70 are adjacent the surfaces of MSR 20 and obscured by panel 71 when viewed from the cancellation volume 25. In some embodiments the wire paths 70 are embedded in surfaces of the MSR 20. However, coil panel 5 may also be arranged with the wire paths 70 exposed and facing the cancellation volume 25. The surface of supporting panel 71 may, in some embodiments, be covered to protect or to simply obscure the unit coil.

Certain coil parameters are determined, which in the present embodiment are the symmetrical side lengths 72, 73 of each coil square 70, a regular spacing between coil centres 79, and the distance of the centre of the 2×2 grid from the centre of each surface of the MSR. For a given set of coil parameters, the magnetic field generated by a unit of applied current in each coil over a regular grid of 'target points' spanning a volume of interest is calculated. The magnetic field calculation may incorporate data relating to interactions with the nearby mu-metal of the surfaces of the MSR 20. Each target point is determined as before.

Figures 7B, 7C:
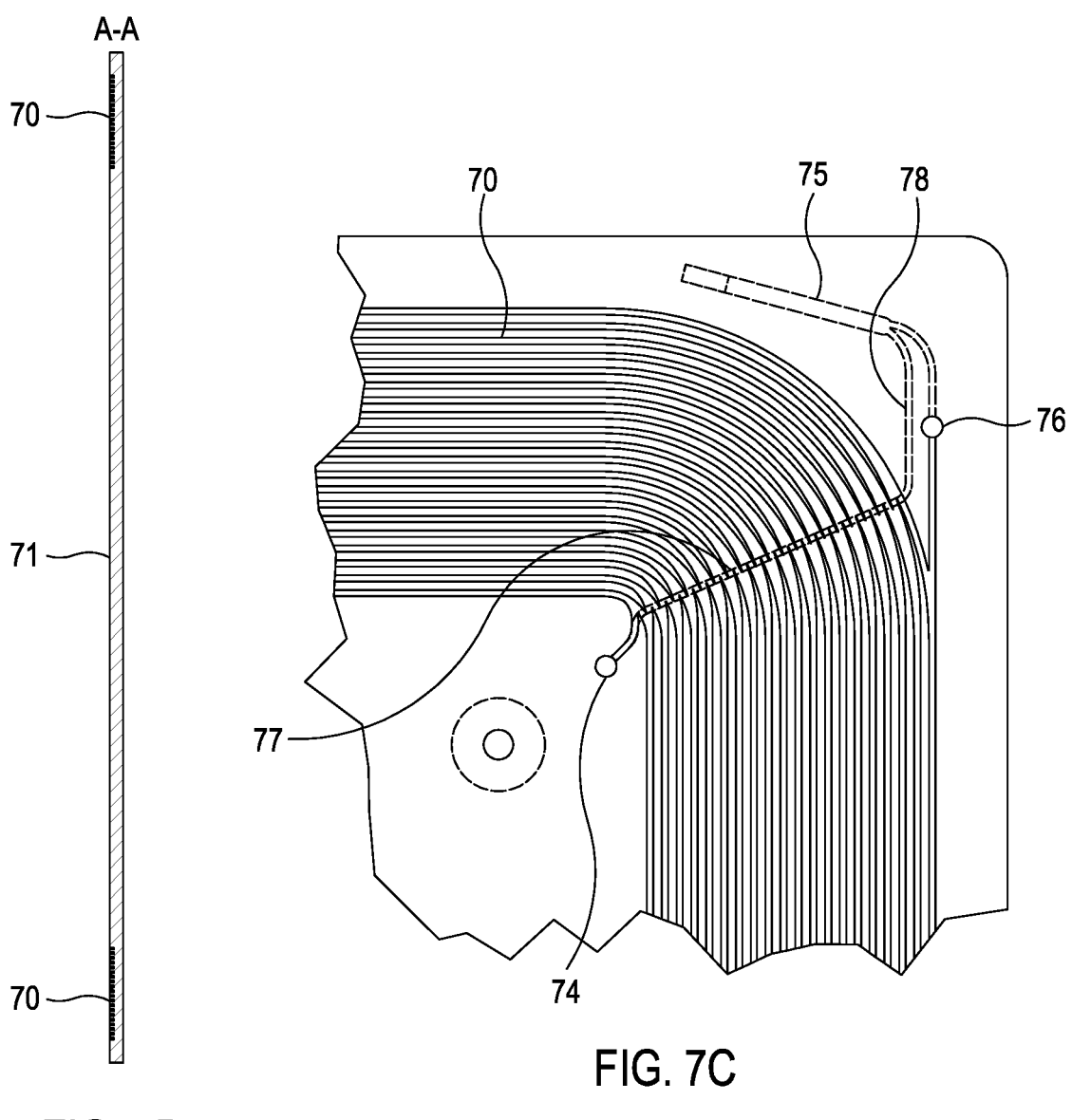
FIG. 7B is a section view of the fifth coil panel of FIG. 7A.
FIG. 7C is a cut away section view of an arrangement of coils of the fifth coil panel of FIG. 7A.

FIG. 7B is a section view of the fifth coil panel 5 of FIG. 7A. Coil wire path 70 is shown as recessed into the planar surface of supporting panel 71. Supporting panel 71 is formed of a plastic or wood material.

In some embodiments, the supporting panel may be formed of an appropriate material such that the supporting panel provides passive shielding.

The unit coil windings of coil wire path 70 are typically recessed to a depth of 3 mm, and remain visible on the first planar surface of supporting panel 71. Each successive winding is offset from the previous at 2 mm, with each of the wires of wire path 70 being typically 1.5 mm diameter.

FIG. 7C is a cut away section view of the coil wire path 70 of the fifth coil panel 5 of FIG. 7A showing the coil wire path 70 and associated connections. The coil wire path 70 is formed of a single winding arranged around the periphery of the planar surface of supporting panel 71 such that that each successive winding is adjacent the previous iteration. The coil wire path 70 of the present embodiment is formed of 20 windings extending between coil terminal 74 and coil terminal 76.

A coil bridging section 77 extends between coil terminal 74 and coil terminal 76. An external connector 75 connects both coil terminal 36 and coil bridging section 77 to an external current source, the latter being connected via coil bridging connector 78.

The external current source is arranged to provide a set of current values such that the coils of coil wire path 70 produce arbitrary vector magnetic field patterns in accordance with the current applied to each of the unit coils.

Figure 7D:
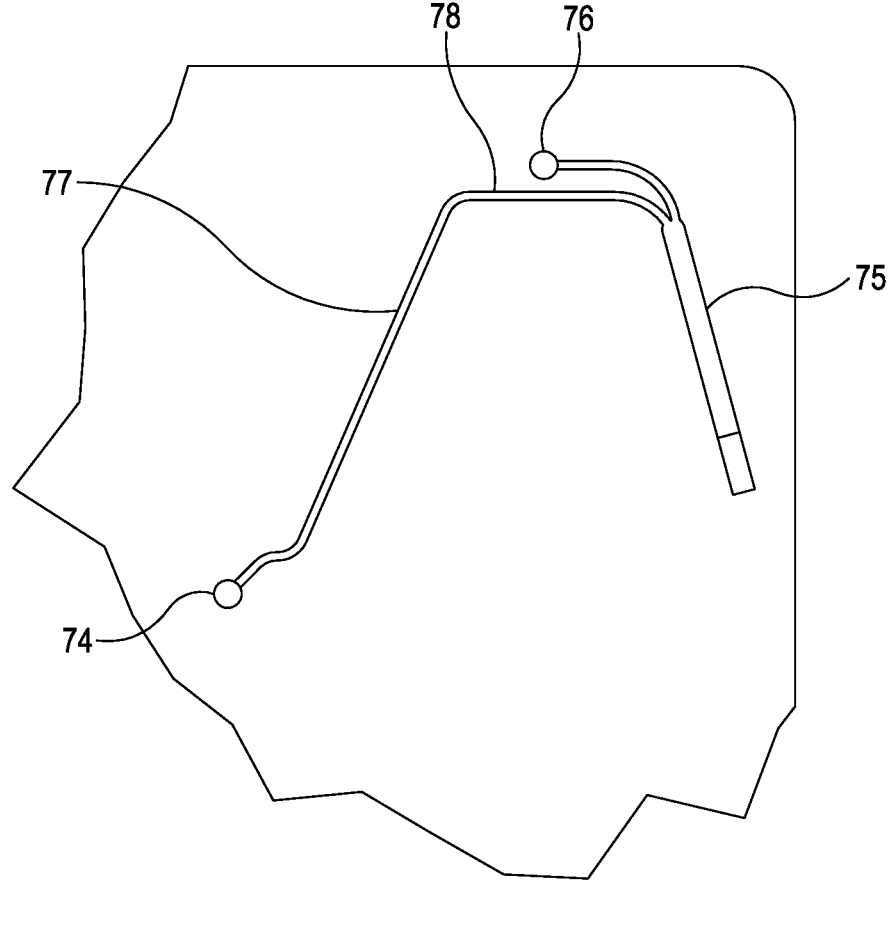
FIG. 7D is a cut away section view of the coil connections of the fifth coil panel of FIG. 7A.

FIG. 7D is a second planar view of the coil connections of the fifth coil panel 5 of FIG. 7C. The coil terminals 74, 76, coil bridging section 77, coil bridging connector 78 and external connector 75 are located on a second planar face of the supporting panel 71 opposite the first. The coil wire path 70 is located on the first planar surface such that only the components located on the second planar face of supporting panel 71 are visible and/or accessible. In embodiments in which the coil wire path 70 is on a planar face of supporting panel 71 visible from inside the cancellation volume 25 of magnetically shielded room 20, the coil terminals 74, 76, coil bridging section 77, coil bridging connector 78 and external connector 75 are located on the same planar face as that of the coil wire path 70.

Figure 8A:
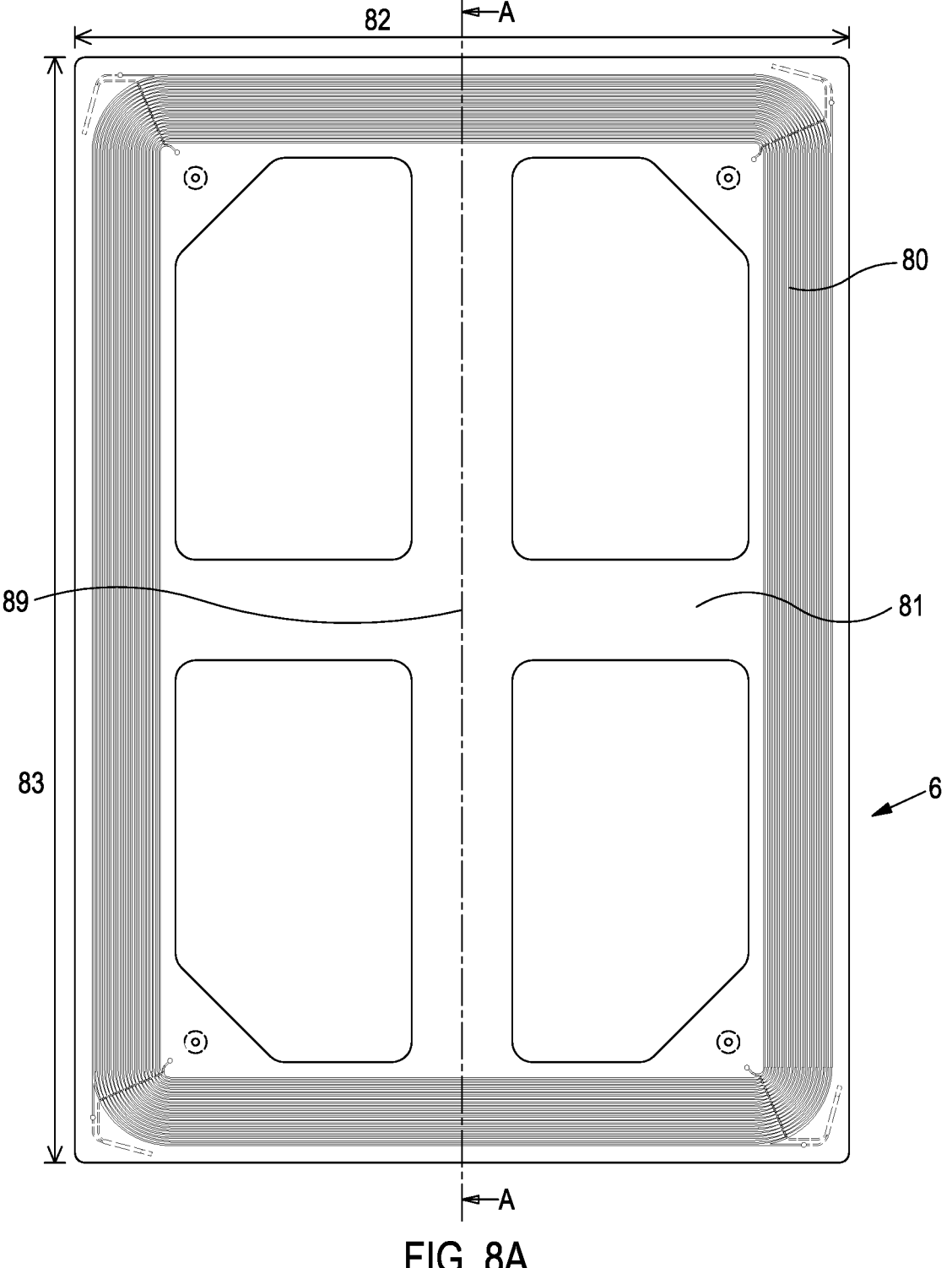
FIG. 8A is a planar view of a sixth coil panel in accordance with the invention.

FIG. 8A is a planar view of a sixth coil panel 6 in accordance with the invention. Coil panel 6 shown in planar view. Coil wire path 80 is affixed to a first planar surface of supporting panel 81. Coil wire path 80 extends adjacent the periphery of the planar surface of supporting panel 81 in a rectangular shape to fit within the surface area of the panel, which is also rectangular in the present embodiment. The supporting panel 81 has a panel side width 82 that is shorter in length than panel side length 83. Consequently, the section of the coil wire path 80 that extends adjacent panel side length 83 extends over a greater length than the section of the coil wire path 40 that extends adjacent panel side width 82.

The coil wire path 80 extends along a first panel side width 82, a first panel side length 83, a second panel side width 82, and a second panel side length 83 to form a rectangular footprint. The coil wire path 80 is a continuous winding formed or either a discrete piece or several pieces joined to form a singular wire that is repeatedly wound to form a coil of adjacent sections.

Coil panel 6 is mounted such that wire path 80 is adjacent the surfaces of MSR 20 and obscured by panel 81 when viewed from within the cancellation volume 25. In some embodiments the wire paths 80 are embedded in surfaces of the MSR 20. However, coil panel 6 may also be arranged with the wire paths 80 exposed and facing the cancellation volume 25.

The relevant coil parameters are determined, which in the present embodiment are the side width 82 and side length 83 of each coil wire path 80, regular spacing between coil centre 89 and the centres of adjacent coils, and the distance of the centre of the 2×2 grid from the centre of each surface, arranged in three planes. For a given set of coil parameters, the magnetic field generated by a unit of applied current in each coil over a regular grid of 'target points' spanning the cancellation volume 25 is calculated.

Figures 8B, 8C:
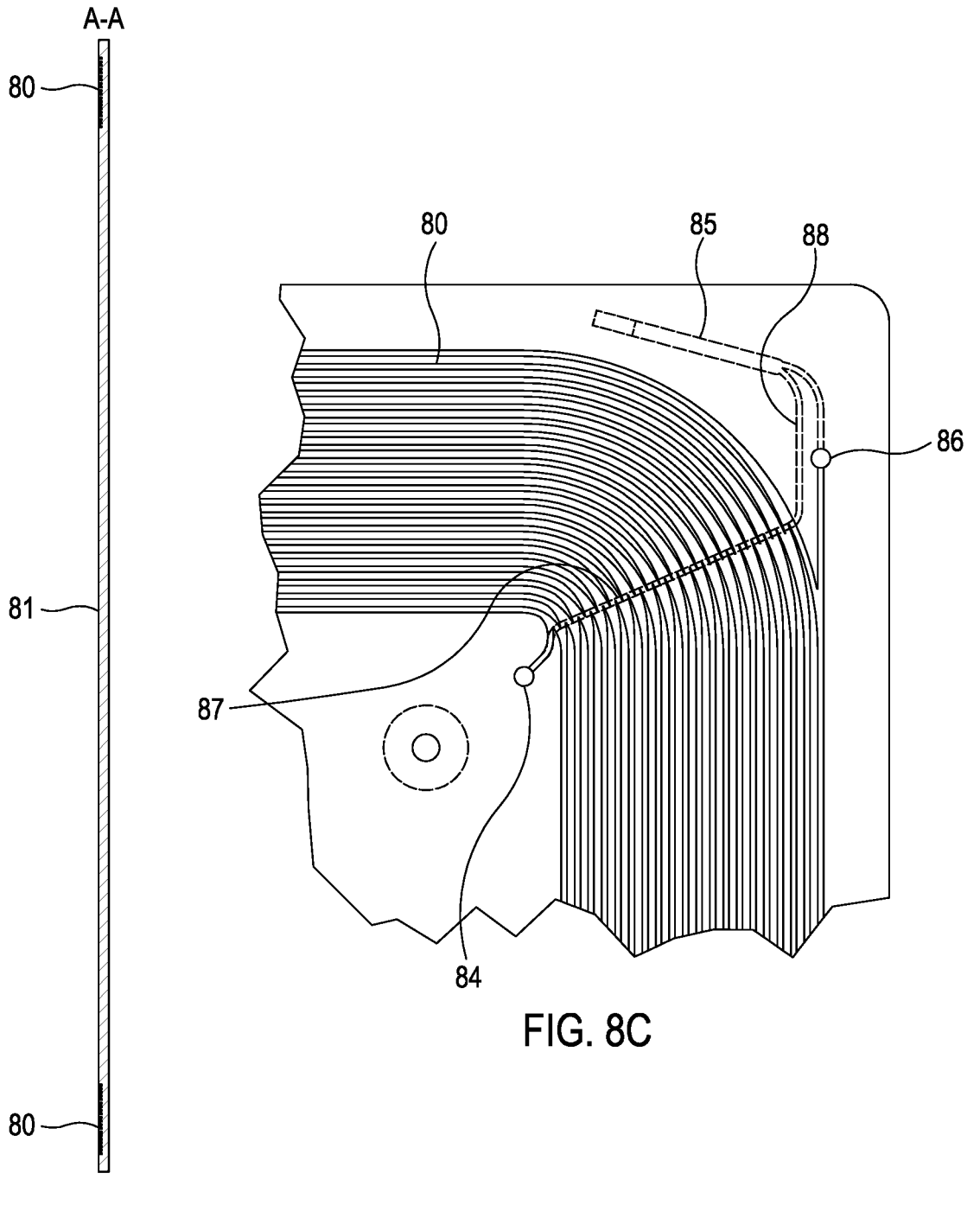
FIG. 8B is a section view of the sixth coil panel of FIG. 8A.
FIG. 8C is a cut away section view of an arrangement of coils of the sixth coil panel of FIG. 8A.

FIG. 8B is a section view of the second coil panel of FIG. 8A, in which supporting panel 81 is shown in cross section. Coil wire path 80 is shown as recessed into the planar surface of supporting panel 81. The windings of coil wire path 80 are typically recessed into the surface of supporting panel 81 and remain visible on its first planar surface. Each successive winding is offset from the previous in a coil wire path having a single layer.

FIG. 8C is a cut away section view of the coil wire path 80 of the sixth coil panel 6 of FIG. 8A showing the coil wire path 80 and associated connections. The coil wire path 80 is formed of a single winding arranged around the periphery of the planar surface of supporting panel 81 such that each successive winding is adjacent the previous. The coil wire path 80 of the present embodiment is formed of 20 windings extending between coil terminal 84 and coil terminal 86.

A coil bridging section 87 extends between coil terminal 84 and coil terminal 86. An external connector 85 connects both coil terminal 86 and coil bridging section 87 to an external current source. The coil bridging section 87 is connected to the external connector 85 via coil bridging connector 88.

Figure 8D:
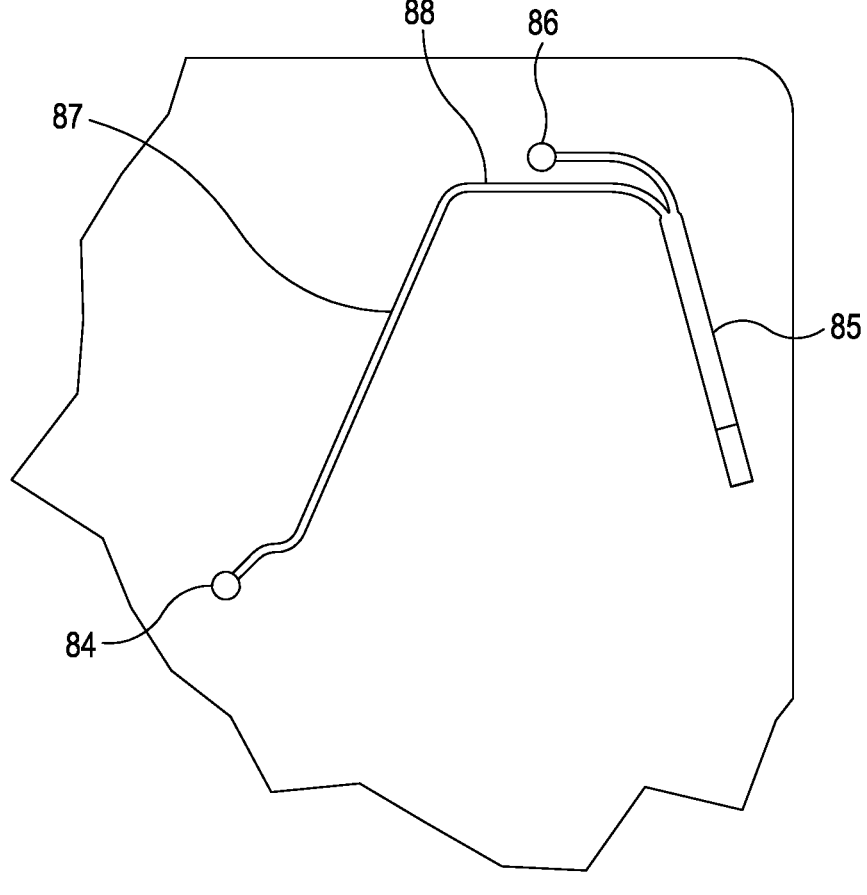
FIG. 8D is a cut away section view of the coil connections of the sixth coil panel of FIG. 8A.

FIG. 8D is a second planar view of the coil connections of the sixth coil panel, coil panel 6, of FIG. 8C. The coil terminals 84, 86, coil bridging section 87, coil bridging connector 88 and external connector 85 are located on a second planar face of the supporting panel 81 opposite the first. The coil wire path 80 is located on the first planar surface such that only the components located on the second planar face of supporting panel 81 are visible and/or accessible.

Figure 9A:
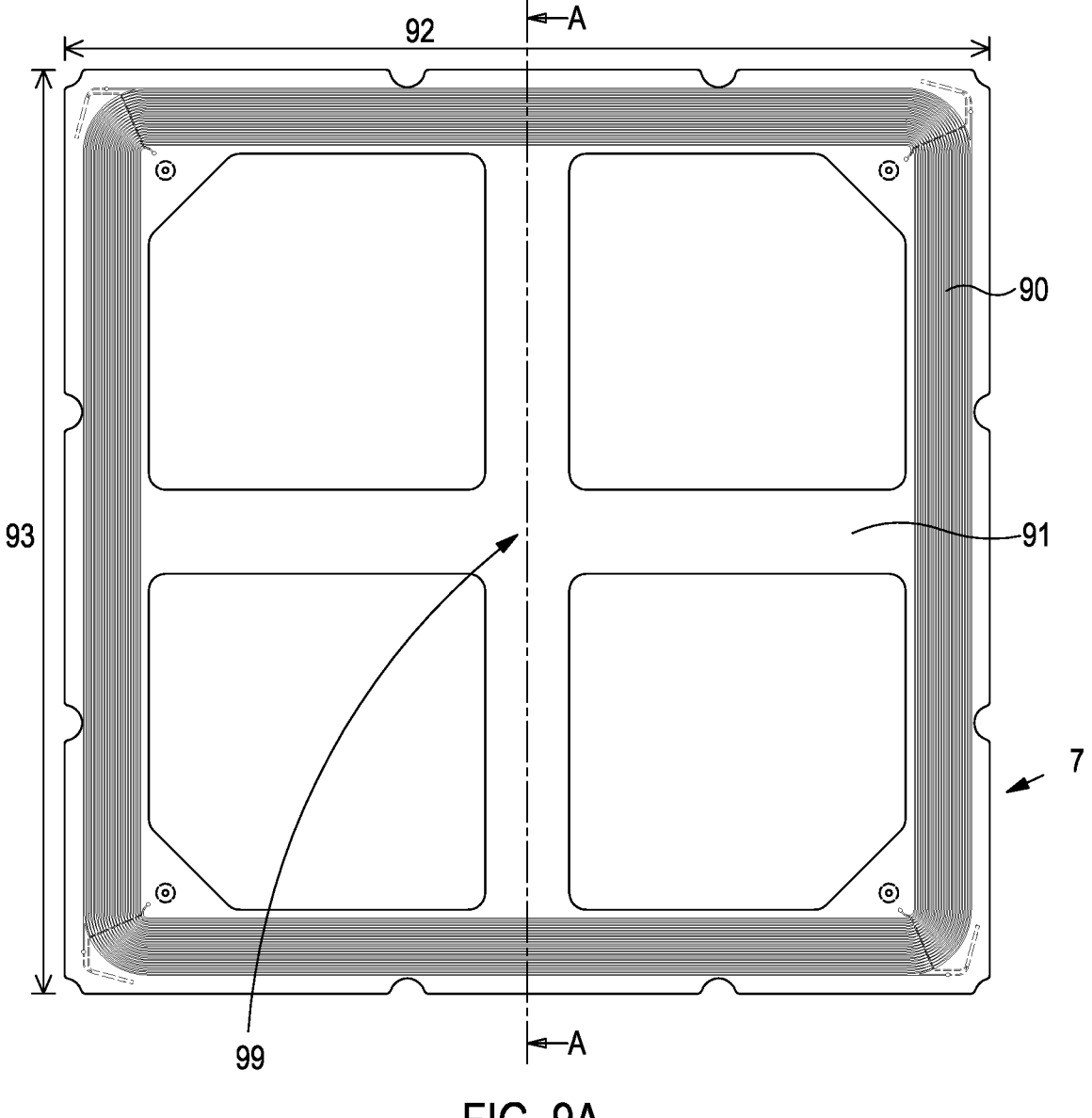
FIG. 9A is a planar view of a seventh coil panel in accordance with the invention.
Figure 10:
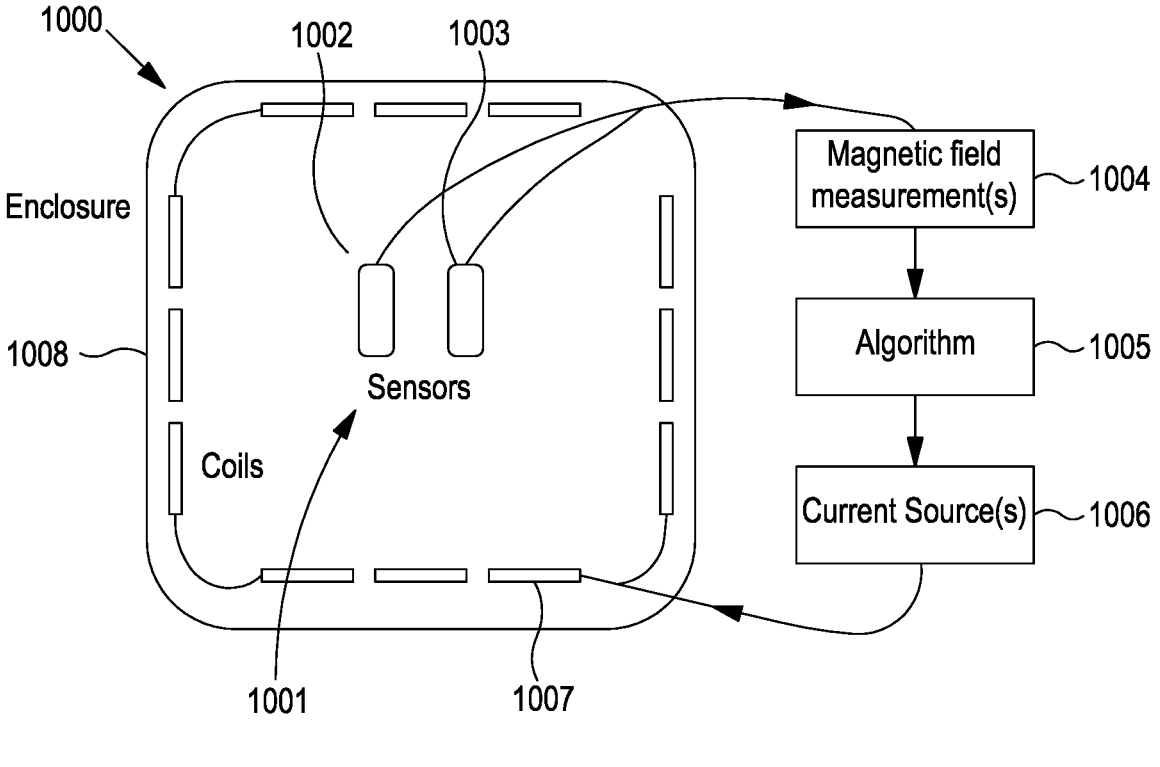
FIG. 10 is a representation of an exemplary window coil system in accordance with the invention.

FIG. 9A is a planar view of a seventh coil panel 7 in accordance with the invention. Coil panel 7 is shown in planar view. Coil wire path 90 is affixed to a first planar surface of supporting panel 91. Coil wire path 90 extends around the periphery of the planar surface of supporting panel 91 in a square shape to fit within the surface area of the panel, which is also a regular quadrilateral in the present embodiment. The coil wire path 90 extends along each panel side length 92, 93 which are substantially equal. The coil wire path 90 is a continuous winding formed or either a discrete piece or several pieces joined to form a singular wire that is repeatedly wound to form a coil of adjacent sections.

Coil panel 7 is arranged such that wire paths 90 are adjacent the surfaces of MSR 20 and obscured by panel 91 when viewed from the cancellation volume 25. In some embodiments the wire paths 90 are embedded in surfaces of the MSR 20. However, coil panel 7 may also be arranged with the wire paths 90 exposed and facing the cancellation volume 25. The surface of supporting panel 91 may, in some embodiments, be covered to protect or to simply obscure the unit coil.

Certain coil parameters are determined, which in the present embodiment are the symmetrical side lengths 92, 93 of each coil square 90, a regular spacing between coil centres 99, and the distance of the centre of the 2×2 grid from the centre of each surface of the MSR. For a given set of coil parameters, the magnetic field generated by a unit of applied current in each coil over a regular grid of 'target points' spanning a volume of interest is calculated. The magnetic field calculation may incorporate data relating to interactions with the nearby mu-metal of the surfaces of the MSR 20.

Figures 9B, 9C:
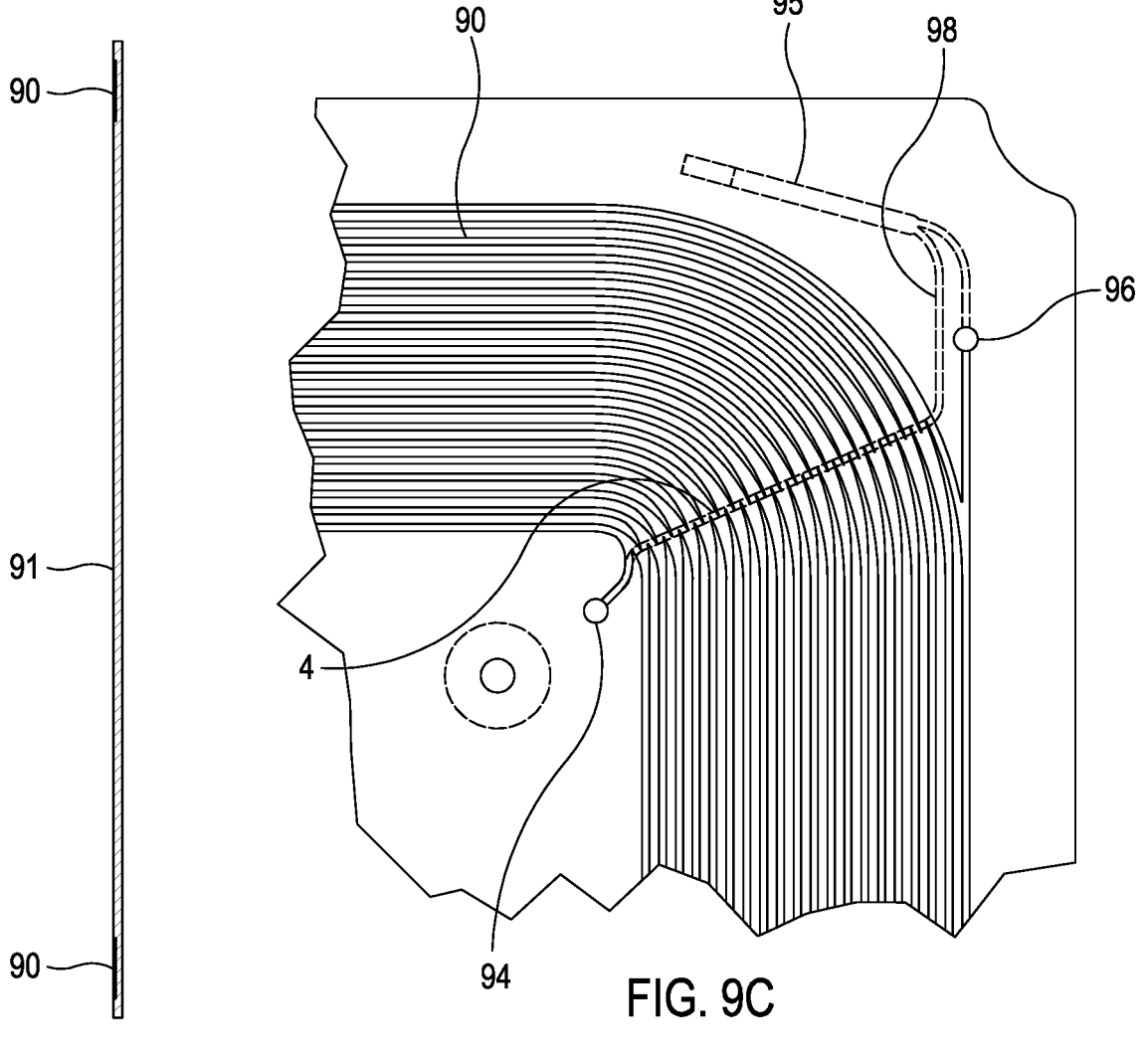
FIG. 9B is a section view of the seventh coil panel of FIG. 9A.
FIG. 9C is a cut away section view of an arrangement of coils of the seventh coil panel of FIG. 9A.

FIG. 9B is a section view of the seventh coil panel 7 of FIG. 9A. Coil wire path 90 is shown as recessed into the planar surface of supporting panel 91. Supporting panel 91 is formed of a non-metallic material. However, in some embodiments, the supporting panel may be formed of an appropriate material such that the supporting panel provides passive shielding.

The unit coil windings of coil wire path 90 are typically recessed to a depth of 3 mm, and remain visible on the first planar surface of supporting panel 91. Each successive winding is offset from the previous at 2 mm, with each of the wires of wire path 90 being typically 1.5 mm diameter.

FIG. 9C is a cut away section view of the coil wire path 90 of the seventh coil panel 7 of FIG. 9A showing the coil wire path 90 and associated connections. The coil wire path 90 is formed of a single winding arranged around the periphery of the planar surface of supporting panel 91 such that that each successive winding is adjacent the previous iteration. The coil wire path 90 of the present embodiment is formed of 20 windings extending between coil terminal 94 and coil terminal 96.

A coil bridging section 97 extends between coil terminal 94 and coil terminal 96. An external connector 95 connects both coil terminal 96 and coil bridging section 97 to an external current source, the latter being connected via coil bridging connector 98.

The external current source is arranged to provide a set of current values such that the coils of coil wire path 90 produce arbitrary vector magnetic field patterns in accordance with the current applied to each of the unit coils.

Figure 9D:
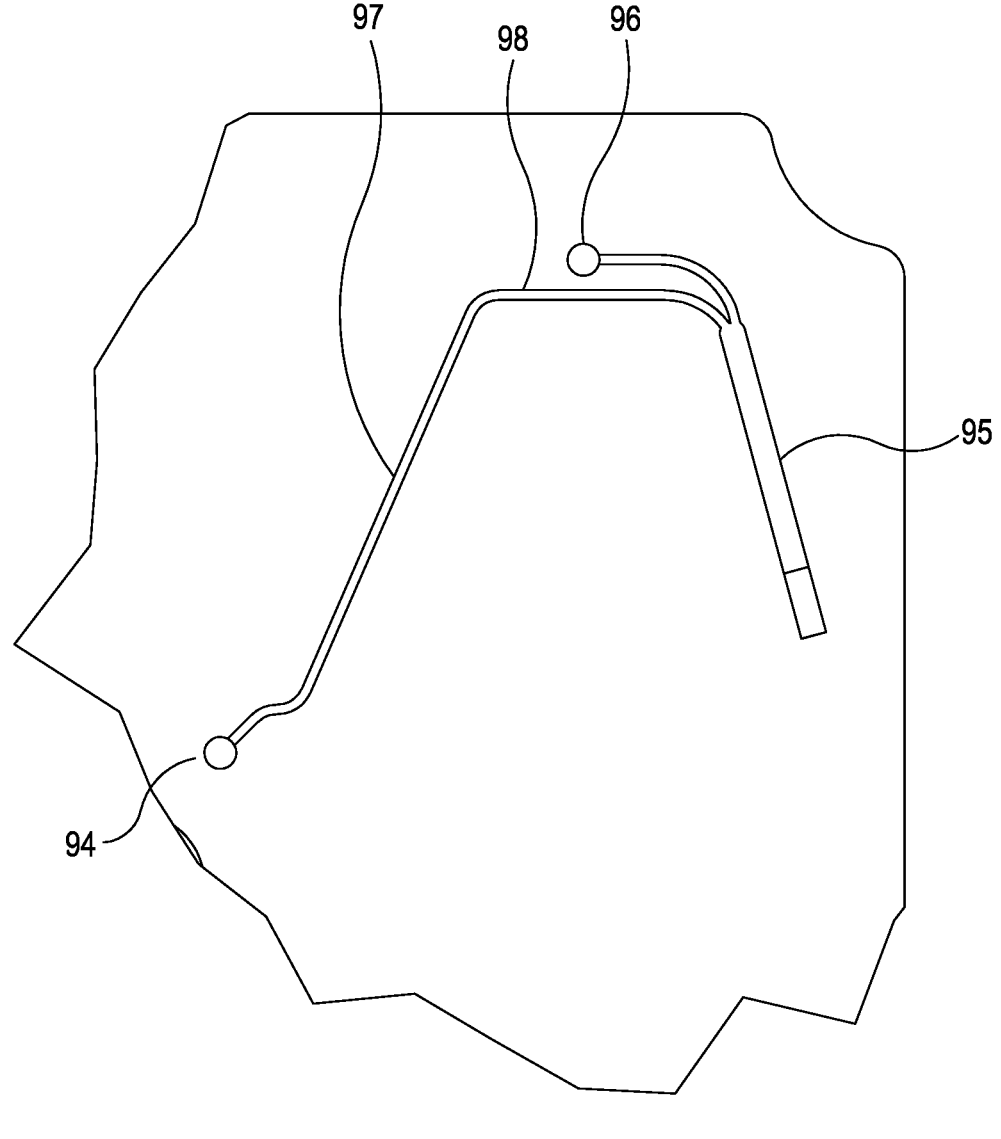
FIG. 9D is a cut away section view of the coil connections of the seventh coil panel of FIG. 9A.

FIG. 9D is a second planar view of the coil connections of the seventh coil panel 7 of FIG. 9C. The coil terminals 94, 96, coil bridging section 97, coil bridging connector 98 and external connector 95 are located on a second planar face of the supporting panel 91 opposite the first. The coil wire path 90 is located on the first planar surface such that only the components located on the second planar face of supporting panel 91 are visible and/or accessible. In embodiments in which the coil wire path 90 is on a planar face of supporting panel 91 visible from inside the cancellation volume 25 of magnetically shielded room 20, the coil terminals 94, 96, coil bridging section 97, coil bridging connector 98 and external connector 95 are located on the same planar face as that of the coil wire path 90.

The supporting panel 91 is for a floor surface of an MSR 20. Typically, the underlying floor is formed of the building foundation, with mu-metal and conductive layers. The supporting panel 91 will typically be obscured by a finished floor covering. The supporting panel 91 has notches thereinto accommodate bolts or other fixings that can extend through the multiple layers of the floor so that the finished floor covering is coupled to the building foundation.

FIG. 10 is a representation of the circuitry of an active magnetic shield system in accordance with the present invention. In the exemplary window coil system 1000, a sensor array 1001 is placed adjacent unit coil 1007. In the present embodiment, the sensor array 1001 comprises sensor 1002 and sensor 1003, and is arranged centrally within enclosure 1008 defining a cancellation volume.

The sensors can be located at any position within the coil enclosure, as the window coils adapt to the change in location. The location will be selected based on the size of the volume to be shielded and the complexity of the field which is measured. Typically, three or more measurements of the full vector of the magnetic field are required, which can be made by three tri-axial magnetic field detectors or nine magnetic field detectors measuring a single component of the magnetic field vector.

Sensor array 1001 is arranged to provide magnetic field measurements 1004 that are processed by algorithm 1005 to determine a current output from at least one current source 1006. The current output is fed to unit coil 1007 to generate an active magnetic shield in enclosure 1008, which, in some embodiments, will be a formed of a passive magnetic shield.

The active magnetic shield is generated by providing an array of magnetic field elements as described herein, each magnetic field element comprising a unit coil 1007, each unit coil comprising a wire path as herein described. A set of coil parameters are specified in each of the unit coils 1007 to which current is applied by current source 1006 to correspond with a grid of target points spanning the target volume of enclosure 1008. The field per unit current generated by each of the unit coils 1007 at each target point is calculated. The calculated field per unit current is mapped to a target magnetic field, and optimal coil currents for each of the unit coils is determined.

In a preferred embodiment, the target magnetic field is derived from magnetic field measurements 1004 provided by sensor 1002 and 1003 of sensor array 1001. The magnetic field generated is compared to the target magnetic field.

However, the desired target field can be either a predetermined field, or can be based on sensed data from the magnetic field sensors 1002, 1003.

In a preferred embodiment, optimal coil currents are determined by minimising the sum of the current values and applying a threshold value to define a maximum value of applied current. The field per unit current produced by each unit coil 1007 at each magnetic field sensor 1002, 1003 is calculated using its known target point position.

The field per unit current produced by each unit coil 1007 at each magnetic field sensor 1002, 1003 is measured by applying a known current to each coil in turn.

The coil parameters in each of the unit coils 1007 is based on unit coil geometry and offset between unit coils. The coil parameters in each of the unit coils can be varied according to the comparison between the active magnetic field generated and the target magnetic field.

Where the magnetic field generated is compared to the target magnetic field and the resultant data does not meet a required threshold, the coil parameters can be varied and a modified magnetic field generated, which is then compared to the target magnetic field. If the mismatch between the modified magnetic field exceeds a threshold value, the process may be repeated until the magnetic field generated and the target magnetic field match, fall within a preferred range, or fall within a threshold value.

The objective of coil current optimisation is to minimise the total power dissipated over the system by keeping the sum of the current values as low as possible. A threshold value is set to determine the maximum applied current and ensure the window coil array operates with physically realisable power supplies.

Following this constrained optimisation, the quality of the solution is evaluated based on the accuracy of the simulated system. The coil parameters, which are, in the present embodiment, square side length, offset between coil centres, and offset of the grid centres, are varied until an optimal set of parameters is found based on the desired target field.

It is desirable to produce many different target fields at each target point. The optimisation is repeated to find a single set of coil parameters which produce field components at all regions where shielding is required. In a preferred embodiment, at least eight field components are produced; three uniform fields and five field gradients.

Traditional coil wire paths are designed to generate a single known component of magnetic field, a field in the x, y or z direction. In the invention disclosed herein, the set of current values required in the coils to generate arbitrary vector magnetic field patterns are calculated and applied. The window coil system essentially 're-designs' itself to produce a different field. The flexibility afforded by the window coil system allows the shielded volume to be sited anywhere in the MSR, and can be updated dynamically to compensate for changing external interference or to 'track' a participant as they move about the MSR. None of this is possible with traditional systems capable of producing fixed field patterns without physically translating the coils.

The participant situated in the MSR 20 may be monitored using a system based on an array of optically pumped magnetometers (OPMs), typical worn by the participant for producing an anatomical scan of the subject's head. These magnetic field sensors can record biomagnetic signals without the application of cryogens for sensor cooling. Each OPM sensor contains a glass cell containing 87Rb vapour, heated to about 150° C. A 795-nm laser beam is used to spin-polarize the atoms, and the intensity of light transmitted through the cell is detected using a photodiode. In zero magnetic field conditions, the spin magnetic moments align with the laser beam, and transmission of laser light is maximized. The presence of a magnetic field perpendicular to the beam causes a measurable drop in light transmission, hence the need for additional shielding in a traditional MSR 20. The OPM sensors have a noise level comparable to that of a SQUID and a dynamic range of +5 nT.

Operation of the shielding system of the present invention requires an array of magnetic field sensors, a controllable current source for each coil in the array, and a feedback algorithm to compute optimal currents. The data collected from the array of magnetic field sensors is used to determine the current applied to each of the magnetic field elements to produce a desired field output.

In practice, the field per unit current produced by each coil at each magnetic field element can be calculated using its known position inside the MSR, or measured by applying a known current to each coil in turn. The resulting values of field per unit current can then be used to find the coil currents which generate a desired response at each of the magnetic field sensors. Example responses include driving all outputs to zero for magnetic shielding, but the same approach is also able to produce a known magnetic field over the array. This ability to produce a known magnetic field over the array is particularly useful for experiments investigating how systems interact with magnetic fields, or in techniques such as Magnetic Resonance Imaging (MRI).

The current calculation method may be arranged to accommodate interference in the form of interactions with the passive shield material into account, to increase the quality of shielding. The number of coils, along with their shapes, sizes, and positions can be optimised for each enclosure, or space to be shielded, to ensure good cancellation in the relevant size and shape cancellation volume, unlike traditional systems that are only capable of producing fixed field patterns.

The arrangement disclosed herein can reduce the magnetic field over a volume equivalent to the average head size within a MSR from ~5 nT to <0.2 nT, therefore providing an ultra-low magnetic field environment suitable for OPM-MEG applications. This system therefore increases typical reduction of the Earth's magnetic field from 10,000 times in conventional MEG MSRs to 250,000 times. This reduction will allow OPM-MEG to be used in neuroscience applications in which multiple subjects can be scanned simultaneously, and following real-time face-to-face interactions between adults, or of parents with their children, investigating spatial navigation.

The clinical applications include, for example, the long-term monitoring of epileptic activity, where remaining still in a traditional system would be impractical and uncomfortable. When the magnetic field sensor rotates or translates, it measures a change in magnetic field equivalent to the size of the magnetic field it is operating in. This part of the data contains no brain information and is therefore undesirable. The system described herein reduces the field, consequently reducing the size of unwanted artefacts in the data, allowing larger subject motions without signal loss.

Figure 11:
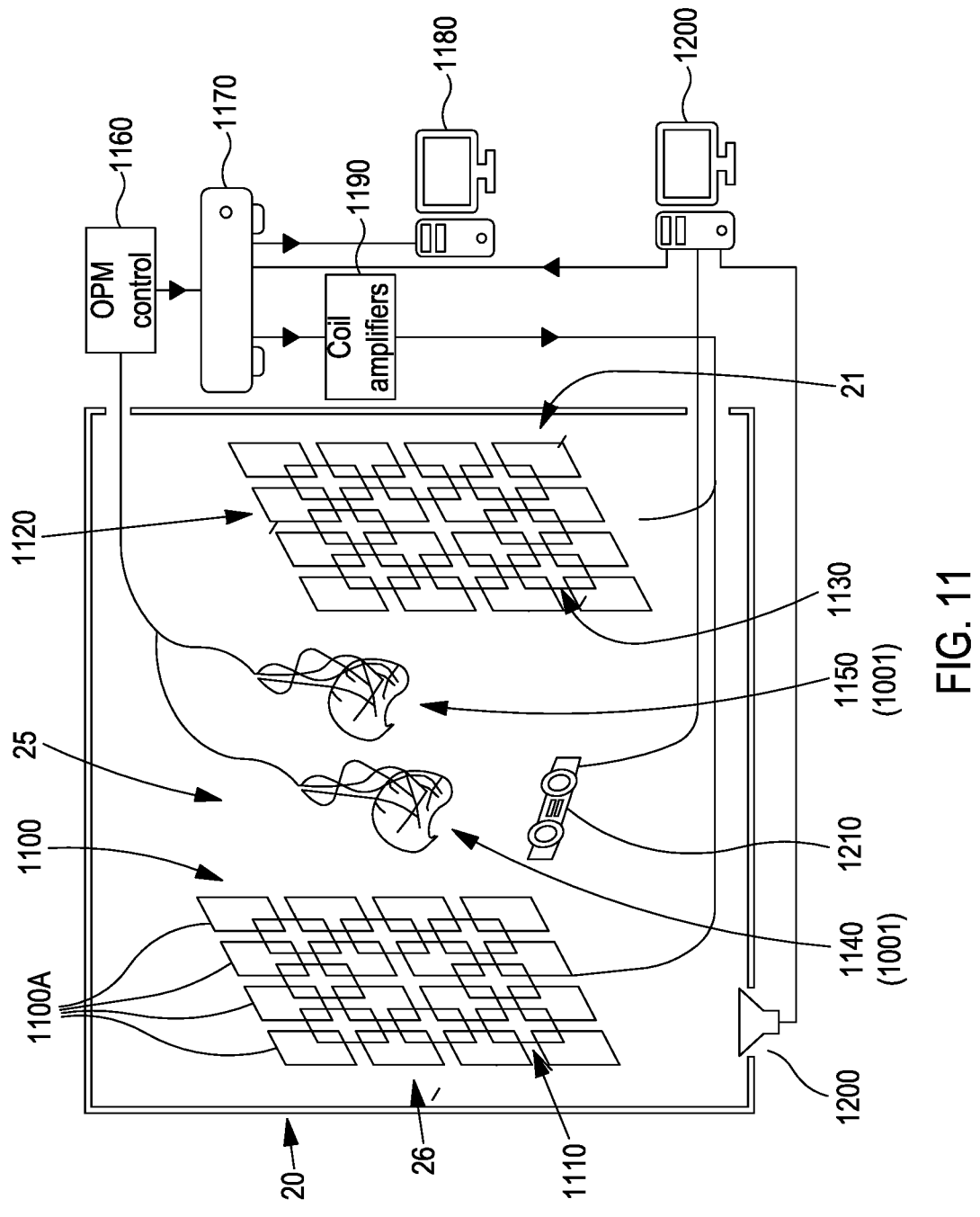
FIG. 11 is a representation of an embodiment of a window coil system in a matrix configuration in accordance with the invention.

FIG. 11 shows a further embodiment of the window coil system in according with the present invention, and shows a representation of a window coil system in a matrix configuration.

A magnetically shielded room 20, forming a passive shield as previously described herein, is provided. The active magnetic shield provided within the passive shield 20 to null remnant magnetic fields within the passively shielded space comprises a number of coil panels having wire paths provided thereon, as disclosed previously.

A first set of coil wire paths 1100, 1110 are placed on wall surface 26. A second set of coil wire paths 1120, 1130 are placed on wall surface 21. The wall surface 21 is arranged opposite and parallel to wall surface 26, to define opposing sides of a cancellation volume 25. The two sets of coil wire paths 1100, 1110, 1120, 1130 form an active magnetic shield within the passively shielded room 20.

The first set of coil wire paths 1100 is comprised of four rows of four wire paths 1100A, 1100B, 1100C, 1100D. Each of the coil wire paths of the first set of coil wire paths 1100 is arranged as per the previous embodiments of window coils described with respect to FIGS. 2 to 10, in that the coils are arranged in a single plane in a grid pattern. The coils are arranged adjacent one another in both a vertical and a horizontal direction.

The first set of overlapping coils 1120 comprises eight coils arranged such that each of the eight coils overlies a central intersection of a 2×2 grid of coils of first coil wire path 1100 affixed to wall surface 26. Although the coils are arranged in a bi-planar arrangement, the presence of the overlapping coils results in the generation of magnetic fields in the x, y, and z planes, unlike Helmholtz coil systems.

Likewise, the second set of coil wire paths 1120 is comprised of four rows of four wire paths 1120A, 1120B, 1120C, 1120D. Each of the coil wire paths of the second set of coil wire paths 1120 are arranged in a single plane in a grid pattern. The coils are arranged adjacent one another in both a vertical and a horizontal direction. The second set of overlapping coils 1130 comprises 8 coils arranged such that each of the eight coils overlies a central intersection of a 2×2 grid of coils of second coil wire path 1120 affixed to wall surface 21.

The specific arrangement of the active magnetic shielding system of the present embodiment is set out in FIG. 11.

Data acquisition unit 1170 is arranged to receive sensor data from the OPM sensor control unit 1160. The data acquisition unit 1170 typically comprises software that allows measurement and/or control of electrical or physical parameters, such as voltage, current, temperature, pressure, and sound, utilised or detected by sensor arrays 1001. In the present embodiment, the data acquisition unit comprises a computer processor with programmable software arranged to receive information from the sensors, and signal conditioning elements.

In the preferred embodiments disclosed herein, each OPM sensor is preferably a small integrated unit incorporating a heated glass cell containing a vapor of rubidium atoms, a 795-nm wavelength diode laser tuned to the D1 transition of rubidium, and a photodetector. Following optical pumping, at zero magnetic field, the rubidium atoms are insensitive to photons of polarised laser light. The intensity of the light which passes through the cell to the photodetector is therefore at a maximum. Changes in the magnetic field experienced by the cell result in a decrease in the measured laser intensity as photons are absorbed by the atoms. The photodetector signal can therefore be used as a sensitive measure of magnetic field. OPMs typically measure in two planes transverse to one another. However, other suitable known vector magnetic field sensors may also be used.

Data from the sensor array 1001 is used to drive the matrix coil field nulling process before a MEG recording begins. Optical tracking records the movement of the participant during MEG recoding. The location of the sensor arrays 1001 of a first set of target points 1140 and a second set of target points 1150 are used to provide data on the locations of and conditions at the sensors during measurement. A single cluster of target points may be utilised, or multiple clusters of target points may be utilised, each providing a discrete set of measurements relating to the subject, or participant, to which they are affixed. The data acquisition unit 1170 provides data to a control PC 1180 and to coil amplifiers 1190.

The data acquisition unit 1170 receives information in respect of the stimulus triggers from a stimulus PC 1200, and the stimulus PC 1200 provides data to participants via auditory instruction delivered through speakers 1220.

The stimulus PC 1200 provides data to and receives data from a motion capture system 1210 that records the physical movements of the participant(s) within cancellation volume 25. The participants may be located anywhere within the cancellation volume 25. In the present embodiment, an "Optitrack" system is used but other such known systems that capture all types of human body movement can be used. The motion capture system 1210 captures rigid body movements, including both subtle and fast motions. Body movement is captured via the use of visible markers affixed to the body, which typically number at least three markers visible to the motion capture system 1210. Facial movement, muscular movement, and skeletal movement can be tracked. The location and number of markers will be selected according to the experimental programme undertaken, and in accordance with the stimulus selected.

Each unit coil 1100, 1110, 1120, 1130 is connected to a single output of a 48-channel, low-noise, voltage amplifier, shown as coil amplifiers 1190 in FIG. 11. The number of channels matches the number of coils present in the array. The coil amplifiers 1190 are interfaced to digital to analogue converters in the data acquisition unit 1170.

In the present embodiment, the voltages applied at the amplifier input range between ±10 V. The maximum electrical current in each coil is tuned by an additional series resistance, which was selected as 1.2 kΩ such that the magnetic field noise generated by the coils is below the lower noise threshold of the OPM sensor arrays 1001. The OPM lower noise threshold is typically 15 fT/√Hz in the selected frequency range. The coil driver current noise at this resistance is <10 nA/√Hz in the 1-100 Hz band, which translates to less than 0.1 fT/√Hz noise in the field, simulated from sum of squared vector field components from each coil at substantially the centre of the two wall surface planes 21, 26.

The MSR 20 of the present exemplary experimental programme comprises four layers of mu-metal, one layer of copper, and demagnetisation coils. The typical remnant magnetic field and gradient is of order 2 nT and 2 nT/m, at the centre of the magnetically shielded room 20.

A 48-coil bi-planar matrix coil system is provided, with 24 coils formed of a first set of coil wire paths 1100 and a first set of overlapping coils 1110 on a wall surface 21, and with a further 24 coils formed of a second set of coil wire paths 1120 and a second set of overlapping coils 1130 on a wall surface 26.

In an exemplary experimental programme, the efficacy of the matrix coil system and its effects on the background magnetic field and resulting data quality are evaluated by taking biomagnetic measurements of two participants undertaking a simple ball game. In the exemplary experimental programme, a first and a second participant are placed within cancellation volume 25 between wall surfaces 21, 26 of a magnetically shielded room 20. A first array of target points 1140 formed of a sensor array 1101 is affixed to one participant, and a second array of target points 1150 formed of a sensor array 1101 is affixed to another participant. Each of the arrays of target points 1140, 1150 comprises an array of twelve OPM sensors arranged to capture magnetoencephalography data. The location of the OPMs is selected according to the measurements required and the underlying anatomy of the participants. In other preferred embodiments, each participant can support an array of sixteen OPMs placed over specific anatomical structures (the left sensorimotor cortex, for example) or evenly distributed over the entire head. The number and location of sensors may be varied according to the nature of the data collected and/or magnetoencephalography objectives, and the arrangement and size of the subject/participant.

Each of the participants are equipped with wearable magnetoencephalography comprising sensor arrays 1001 to record electrophysiological data from the brain. High fidelity control of background magnetic fields enables free movement of one or more participants scanned simultaneously such that each participant is scanned separately within the same cancellation space. There is therefore no need to enclose two participants in a single machine, or in separate machines linked by electronic means. As per the window coil arrangement described in respect of FIGS. 2 to 10, unit coils produce a 3D vector magnetic field pattern that can be adjusted or defined within a cancellation volume in accordance with nulling requirements. In embodiments in which a window coil array is arranged with no overlapping coils, there is a need to place coils on all six faces of a cuboidal cancellation volume. The cluster of target points defined by the sensor array can be located anywhere within the shielded volume 25, thus permitting the subject scanned, or participant where more than one subject is present, to move around with the shielded space, allowing multi-person scanning to be carried out simultaneously.

The current in each of the 48 coil wire paths is individually controlled to generate a required field in order to cancel the remnant magnetic field inside the MSR 20 at the location of each of the target sensor arrays 1140, 1150.

A current distribution of −8 to +9 mA was used during the exemplary two-person ball game. The strength of the direct current field, reported by the 48 total field measurements from the sensor arrays 1140, 1150 arranged in respect of each participant Although OPM sensors typically feature 'on-sensor' coils to compensate local static magnetic fields up to ±50 nT, with data measured relative to this offset within a narrow dynamic range of around ±5 nT, any subsequent movement of an OPM with respect to the background field induces a change in the measured magnetic field. This can cause a field shift >5 nT will saturate sensor outputs so that no data can be collected, a change in sensor gain that causes significant inaccuracies in measured data, and/or artefacts caused by rotating the sensor in a field, or translating it in a field gradient that swamps brain activity measurement.

As magnetoencephalography data is corrupted with significant artefacts when the remnant field is not compensated, with active shielding initiated by the coil wire paths, the biomagnetic activity in the sensorimotor regions of each participant is recorded and correlated with the stimulus instructions from stimulus PC 1200, and data from motion capture system 1210.

Participant movements were tracked during the experiments using motion capture system 1210 in which two cameras, each with an array of fifteen infrared LEDs, illuminate infrared reflective markers. The combined coordinates of multiple markers are used participant body tracking with six degrees of freedom (x, y and z translations, pitch, yaw and roll rotations).

"Hyperscanning" offers a means to simultaneously assess brain function in two interacting individuals. Present technologies are extremely limited, either by performance, or unnatural scanning environments, but by providing an overlapping matrix of window coils as described herein, naturalistic hyperscanning is possible. Unlike previous active magnetic shielding systems, such as the Helmholtz coil arrangements which use two planes to create a single field vector, the arrangement of the matrix window coils allows accurate field control anywhere over the cancellation volume surrounded by the coil set. By positioning two spatially separated zero-field regions over OPM sensor arrays worn by interacting subjects, the environment required for the collection of high-quality MEG data in two-person experiments can be achieved. The remnant magnetic field within the cancellation volume can be nulled using the matrix coil system at the locations of both first sensor array 1140 and second sensor array 1150.

Figure 12:
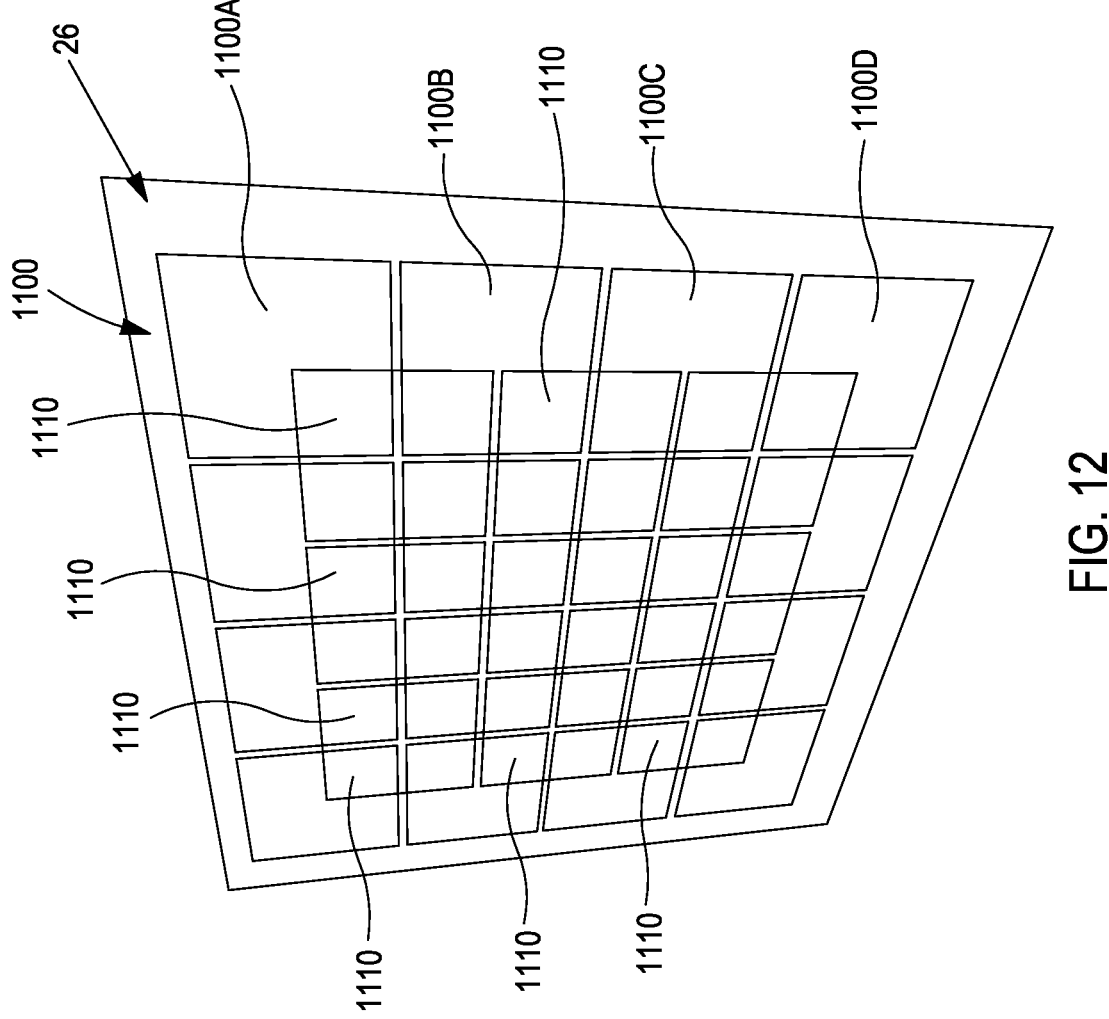
FIG. 12 is a planar view of a window coil panel in a matrix configuration in accordance with a further embodiment of the window coils in a matrix configuration in accordance with the invention.

FIG. 12 is a planar view of one of the two window coil panels arranged in a matrix configuration in accordance with a further embodiment of window coils. As per the arrangement disclosed in FIG. 11, the coil paths are arranged on two surfaces of a MSR 20 but are arranged to produce a 3D vector pattern.

The active shield of the present embodiment comprises two planes, each containing twenty five individually controllable square "window" coils, rather than the twenty four coils of the embodiment of FIG. 11. The overlapping coils 1110, 1130 are arranged in a 3×3 grid such that each of the overlapping coils 1110, 1130 overlies a portion of four of the window coils 110, 1120, the window coils being arranged substantially as described in relation to FIG. 11.

Superposition of the magnetic field generated by the coils, each carrying an independently controllable current, enables the production of arbitrary patterns of magnetic field variation within selected target volume(s) in a 3D vector pattern. In simple terms, the overlapping coils can cancel the fields generated by the underlying window coils arranged in a 4×4 matrix. Finer control of directional cancellation can therefore be achieved in the resulting pattern, which is a resolution of the fields produced by the coil wire paths 1100, 1120 and the overlapping wire paths 1110, 1130. Consequently, a finer resolution is available. The overlapping coil lay out allows for the generation of off-axis vector components making 3 dimensional vector cancellation possible.

In the present exemplary embodiment, a small scale shield is described, in which each coil has a square side length of 38 cm and is formed of ten turns of copper wire. The regular 4×4 grid of the non-overlapping window coil arrangement, that are coil wire paths 1100, 1120, are wound onto each surface 26, 21 respectively. A grid of overlapping coils 1110, 1130 applied to each surface 26, 21 respectively. The coil planes were separated by 150 cm and positioned such that the centre of the coil array was at a height of 130 cm from the floor, with the array spanning a height range of 50 to 210 cm to accommodate a selected range of adult participants.

In embodiments in which overlapping unit coils, such as those shown in FIGS. 11 and 12, are provided in an MSR 20, it is not necessary to place coils on all six surfaces of a cuboidal shielded volume 25. However, providing an overlapping coil array on all six faces of a cuboidal MSR 20 enables a wider variety of magnetic shields to be produced.

The modular nature of the window coil arrangement makes design and construction simpler than that of the intricate wire paths required by distributed coil systems. Whether the window coil arrangement comprises adjacent coils, or a combination of adjacent and overlapping coils, the complexity is shifted from the coils to the coil amplifier and field control systems. The data-driven field cancellation approach accommodates any position of sensor array within the cancellation volume 25, coil layout, and magnetic field distortions caused by the presence of mu-metal in the passive shield where present. The MSR 20 is therefore not limited to a specific shape.

The remnant magnetic field inside the MSR 20 experienced by each sensor in the sensor arrays 1001 (projected along their longitudinal and transverse axes) is measured, along with a calibration matrix containing the magnetic field generated per unit current, at each sensor, by each of the 48 matrix coils. The coil currents that will optimally null the magnetic field experienced by the OPM array are computed.

To null the remnant magnetic field inside the MSR during a magnetoencephalography experiment, the following equation is used. If the magnetic field measured by the $n^{th}$ OPM in an array of N sensors due to unit current in the $m^{th}$ coil in a set of M (=48) matrix coils is written as $db_n/dl_m$, we can form a (N×M) coil calibration matrix, A, from the full set of values. The field nulling problem can then be described using the following matrix equation:

$$\begin{bmatrix} \dfrac{db_1}{dI_1} & \dfrac{db_1}{dI_2} & \cdots & \dfrac{db_1}{dI_M} \\ \dfrac{db_2}{dI_1} & \dfrac{db_2}{dI_2} & \cdots & \dfrac{db_2}{dI_M} \\ \vdots & \vdots & \ddots & \vdots \\ \dfrac{db_N}{dI_1} & \dfrac{db_N}{dI_2} & \cdots & \dfrac{db_N}{dI_M} \end{bmatrix} \begin{bmatrix} I_1 \\ I_2 \\ \vdots \\ I_M \end{bmatrix} = -\begin{bmatrix} b_1 \\ b_2 \\ \vdots \\ b_N \end{bmatrix},$$

$$Ax = -b.$$

Where the (M×1) column vector x contains the currents applied to each coil and the (N×1) column vector b characterises the magnetic field to be cancelled. b is formed using the DC field values measured at the sensors, the negative sign is used to ensure the calculated currents null the magnetic field measured by the array.

The optimal coil currents required to minimise the sum of squares of the measured magnetic field values can be found by identifying the negative of the Moore-Penrose pseudo-inverse matrix of A: $x = -(AA^T)^{-1}A^Tb$.

To minimise the power dissipated by the system, and ensure the solution is physically realisable, the matrix $AA^T$ can be regularised prior to inversion by addition of a matrix $\alpha I$ where I is the identity matrix of the same dimensions as $AA^T$ and $\alpha$ is a regularisation parameter: $x = -(AA^T + \alpha I)^{-1}A^Tb$.

To keep the coil currents within the allowed bounds, the latter equation is cast as a feed-forward controller with the required currents at each timepoint i, related to the currents applied at the preceding time point and the fields measured at the present timepoint:

$$x^i = x^{i-1} - G(AA^T + \alpha I)^{-1} A^T b^i.$$

The gain coefficient G is empirically set to produce a stable reduction of the measured fields towards zero on a timescale of a few seconds.

This system may therefore be adapted to changes in the number and shape of the unit coils and flexibly incorporates multiple sensor arrays 1001, each representing a participant in cancellation volume 25.

Coil calibration data for populating the matrix, A, can be collected in a variety of ways depending on the available sensing technology e.g. by pulsing each coil in turn or by applying a known sinusoidal current to each coil. Values could also be calculated based on known sensor positions, coil design and geometry of the MSR 20.

Participants are typically required to remain still during the nulling process whilst a 5 V (4.16 mA) 100 ms pulse was applied to each coil in turn. The nulled volumes can be placed at any location between the coils, meaning that an experiment can be carried-out with a single subject standing, seated, or with multiple subjects. Nulling has been found by the inventors to decrease the average background field by a factor of between 6 and 10 for a given participant.

The time needed for the calibration process scales with the number of coils and takes around 1a minute to complete for a forty eight coil system. The magnetic field values reported by each sensor prior to calibration are stored, along with the coil calibration matrix, the final voltages applied to each coil, and the final magnetic field values.

The invention can be applied to other applications where magnetic shielding or another form of magnetic field control is required. Outside of diagnostics and medical imaging, the arrangement disclosed herein may be combined with scanners for virtual reality experiences.

It will of course be understood that many variations may be made to the above-described embodiment without departing from the scope of the present invention. For example, cylindrical shields may be used in place of the cuboid shapes described herein. In such instances, a suitable co-ordinate system would be used in place of a standard 3 plane coordinate system.

The invention claimed is:

1. An active magnetic shield system, comprising:
an array of magnetic field sensors arranged to sense a local magnetic field,
an array of magnetic field elements arranged produce a magnetic field of −20 nT to +20 nT, the array of magnetic field elements comprising a first set of unit coils and a second set of unit coils, wherein the first set of unit coils is arranged on a first plane and the second set of unit coils is arranged on a second plane spaced from and opposite the first plane, defining a cancellation volume therebetween;
the first set of unit coils comprising a first plurality of unit coils arranged in at least a 2 by 2 grid in the first plane and at least one further unit coil overlapping the first plurality of unit coils; and
the second set of unit coils comprising a second plurality of unit coils arranged in at least a 2 by 2 grid in the second plane and at least one further unit coil overlapping the second plurality of unit coils;
wherein each unit coil comprises a coil wire path arranged to produce a vector magnetic field pattern,
a current source arranged to provide a controlled current to each unit coil, and a processor configured to perform
a feedback algorithm for controlling the current source for each unit coil to minimise the sensed local magnetic field.

2. An active magnetic shield system according to claim 1, wherein the unit coils are arranged on 4, 5 or 6 planes to define the cancellation volume.

3. An active magnetic shield system according to claim 1, further comprising a passive magnetic shield arranged to support the array of magnetic field elements.

4. An active magnetic shield system according to claim 3, wherein the passive magnetic shield comprises at least a first layer formed of high magnetic permeability material, and a further layer formed of high electrical conductivity material.

5. An active magnetic shield system according to claim 3, wherein the passive magnetic shield comprises a magnetically shielded room (MSR), wherein the array of magnetic field elements is placed on or in each wall of the MSR.

6. An active magnetic shield system according to claim 1, wherein the vector magnetic field pattern has a magnitude of 5 nT or smaller.

7. An active magnetic shield system according to claim 1, wherein each unit coil is a square coil.

8. An active magnetic shield system according to claim 1 for use in magnetoencephalography (MEG).

9. An active magnetic shield system according to claim 1, wherein the at least one further unit coil of the first set of unit coils is arranged such that a coil thereof overlies an intersection defined by the 2 by 2 arrangement of the first plurality of unit coils.

10. An active magnetic shield system according to claim 9, wherein the at least one further unit coil of the second set of unit coils is arranged such that a coil thereof overlies an intersection defined by the 2 by 2 arrangement of the second plurality of unit coils.

11. An active magnetic shield system according to claim 1 wherein the first plurality of unit coils comprises an array of sixteen unit coils and the overlapping at least one further unit coil of the first set of unit coils comprise up to 9 overlapping coils.

12. An active magnetic shield system according to claim 11 wherein the second plurality of unit coils comprises an array of sixteen unit coils and the overlapping at least one further unit coil of the second set of unit coils comprise up to 9 overlapping coils.

13. An active magnetic shield system according to claim 1 wherein the overlapping coils are configured to at least partially cancel the magnetic fields generated by the underlying grid of unit coils to thereby allow for the generation of off-axis magnetic field components, wherein the axis is defined as the direction perpendicular to the first plane and second plane.

14. An active magnetic shield system according to claim 1 wherein the overlapping coils overlie a central intersection defined by the 2 by 2 arrangement of the underlying unit coils.

15. A method of producing an active magnetic shield, the method comprising
generating a magnetic field by
providing an array of magnetic field elements, the array comprising a first set of unit coils and a second set of unit coils, wherein the first set of unit coils is arranged on a first plane and the second set of unit coils is arranged on a second plane spaced from and opposite the first plane, defining a cancellation volume therebetween, the first set of unit coils comprising a first plurality of unit coils arranged in at least a 2 by 2 grid in the first plane and at least one further unit coil overlapping the first plurality of unit coils; and the second set of unit cols comprising a second plurality of unit coils arranged in at least a 2 by 2 grid in the second plane and at least one further unit coil overlapping the second plurality of unit coils;

specifying a set of coil parameters in each of the unit coils, applying current in each of the unit coils over a grid of target points spanning a target volume, calculating a field per unit current generated by each of the unit coils at each target point, mapping the calculated field per unit current to a target magnetic field, determining optimal coil currents for each of the unit coils, and comparing the magnetic field generated to the target magnetic field.

16. A method of producing an active magnetic shield according to claim 15, wherein optimal coil currents are determined by minimising the sum of the current values and applying a threshold value defining a maximum value of applied current.

17. A method of producing an active magnetic shield according to claim 15, wherein the field per unit current produced by each coil at each magnetic field sensor is calculated using its known target point position.

18. A method of producing an active magnetic shield according to claim 15, wherein the field per unit current produced by each coil at each magnetic field sensor is measured by applying a known current to each coil in turn.

19. A method of producing an active magnetic shield according to claim 15, wherein the coil parameters in each of the unit coils is based on unit coil geometry and offset between unit coils.

20. A method of producing an active magnetic shield according to claim 15, further comprising:

varying the coil parameters in each of the unit coils based on the comparison between the magnetic field generated and the target magnetic field, and repeating the steps of claim 15 until the magnetic field generated and the target magnetic field match.

\* \* \* \* \*